United States Patent
Nistico' et al.

(10) Patent No.: US 9,939,426 B2
(45) Date of Patent: Apr. 10, 2018

(54) MARKERS FOR THE EPITHELIAL AND PROLIFERATIVE OR MESENCHYMAL INVASIVE PHENOTYPE OF HUMAN NEOPLASIA

(71) Applicant: ISTITUTI FISIOTERAPICI OSPITALIERI (IFO)—ISTITUTO REGINA ELENA PER LO STUDIO E LA CURA DEI TUMORI, Rome (IT)

(72) Inventors: Paola Nistico', Rome (IT); Francesca Di Modugno, Rome (IT)

(73) Assignee: ISTITUTI FISIOTERAPICI OSPITALIERI (IFO)—ISTITUTO REGINA ELENA PER LO STUDIO E LA CURA DEI TUMORI, Rome (IT)

( * ) Notice: Subject to any disclaimer, the term of this patent is extended or adjusted under 35 U.S.C. 154(b) by 10 days.

(21) Appl. No.: 15/136,874

(22) Filed: Apr. 22, 2016

(65) Prior Publication Data

US 2016/0231312 A1 Aug. 11, 2016

Related U.S. Application Data

(62) Division of application No. 13/816,339, filed as application No. PCT/IB2010/053632 on Aug. 11, 2010, now abandoned.

(51) Int. Cl.
| | | |
|---|---|---|
| *C12Q 1/00* | (2006.01) | |
| *G01N 33/50* | (2006.01) | |
| *C12Q 1/68* | (2018.01) | |
| *G01N 33/574* | (2006.01) | |
| *C07K 14/435* | (2006.01) | |

(52) U.S. Cl.
CPC ........ *G01N 33/5011* (2013.01); *C07K 14/435* (2013.01); *C12Q 1/6886* (2013.01); *G01N 33/5743* (2013.01); *G01N 33/57407* (2013.01); *G01N 33/57415* (2013.01); *G01N 33/57419* (2013.01); *G01N 33/57423* (2013.01); *G01N 33/57434* (2013.01); *G01N 33/57438* (2013.01); *G01N 33/57446* (2013.01); *G01N 33/57449* (2013.01); *G01N 33/57492* (2013.01); *C12Q 2600/118* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

2012/0028252 A1  2/2012 Nistico et al.

FOREIGN PATENT DOCUMENTS

| WO | 2009/150494 | 12/2009 |
| WO | 2012/020281 | 2/2012 |

OTHER PUBLICATIONS

Bria et al. "Human Mena (hMena) and isoforms hMena+11a and hMenadeltaV6, estrogen receptor-beta (ER-B), epidermal growth factor receptor-1 and -2 (EGFR/HER-2) expression as prognostic factors in node-negative Non-Small-Cell Lung Cancer (NSCLS)" *Eur. J. Cancer* 7:514 abstract 9030 (2009).
Di Modugno et al. "Molecular cloning of hMena (ENAH) and its spice variant hMena: Epidermal growth factor increases their expression and stimulates hMena phosphorylation in breast cancer cell lines" *Cancer Res.* 67:2657-2665 (2007).
Di Modugno et al. "The cytoskeleton regulatory protein hMena (ENAH) is overexpressed in human benign breast lesions with high risk of transformation and human epidermal growth factor receptor-2-positive/hormonal receptor-negative tumors" *Clin. Cancer Res.* 12:1470-1478 (2006).
Di Modugno et al. "Human mena protein, a serex-defined antigen overexpressed in breast cancer eliciting both humoral and T-cell immune response" *Int. J. Cancer* 109:909-918 (2004).
Goswami et al. "Identification of invasion specific splice variants of the cytoskeletal protein Mena present in mammary tumor cells during invasion in vivo" *Clin. Exp. Metastasis* 26:153-159 (2009).
Nistico et al. "*Homo sapiens* enabled-like protein variant hMenaDv6 (ENAH) mRNA, complete cds, alternatively spliced" GenBank Database accession No. EU255274.1, nucleotide, two pages (2007).
Nistico et al. "Enabled-like protein variant hMenaDv6 [*Homo sapiens*]" GenBank Database accession No. ABY78022.1 protein, two pages (2007).
Philippar et al. "A Mena invasion isoform potentiates EGF-induced carcinoma cell invasion and metastasis" *Dev. Cell* 15:813-828 (2008).
Pino et al. "Human Mena isoform serves as a marker of epithelial phenotype and sensitivity to epidermal growth factor receptor inhibition in human pancreatic cancer cell lines" *Clin. Cancer Res.* 14:4943-4950 (2008).
Int'l Search Report for PCT/IB2010/053632, four pages, dated Feb. 14, 2011.
Written Opinion for PCT/IB2010/053632, six pages, dated Feb. 14, 2011.
Int'l Preliminary Report on Patentability PCT/IB2010/053632, seven pages, dated Feb. 12, 2013.

*Primary Examiner* — Sean E Aeder
(74) *Attorney, Agent, or Firm* — Nixon & Vanderhye PC

(57) ABSTRACT

The present invention relates to a new Ena/VASP protein isoform, uses thereof, diagnostic methods and kits comprising the same.

20 Claims, 7 Drawing Sheets

A

V6 peptide: AAPASVETPLNSVLGDSSASEPGLQAASQPAETPSQQ

B

C

MARKERS FOR THE EPITHELIAL AND PROLIFERATIVE OR MESENCHYMAL INVASIVE PHENOTYPE OF HUMAN NEOPLASIA

CROSS-REFERENCE TO RELATED APPLICATIONS

This application is a divisional of application Ser. No. 13/816,339, filed Apr. 2, 2013, which is the U.S. national stage of Int'l Application No. PCT/IB2010/053632, filed Aug. 11, 2010.

BACKGROUND OF THE INVENTION

The present invention was granted a foreign filing license issued by the Ministero dello sviluppo economico UIBM, on the 30 Apr. 2010, Protocol number 40718.

The present invention relates to a new Ena/VASP protein isoform, uses thereof, diagnostic methods and kits comprising the same.

Carcinogenesis and progression of a tumour lesion are characterized by different gene expression patterns. These expression patterns are defined by different splice-variants and in particular, alternative splicing events frequently affect genes controlling the cytoskeleton organization in tumour cells (Wang G S, Cooper T A. 2007; Gardina P J et al. 2006).

It has been reported that regulatory pathways controlling actin cytoskeleton dynamics are deregulated in cancer cells, and altered expression of proteins controlling actin polymerization frequently occurs affecting growth, survival and migration of tumor cells (Olson M F, Sahai E. Clin Exp Metastasis. 2009).

Unfortunately, despite the progress related to the understanding of molecular mechanisms underlying the carcinogenesis, there are no molecular markers or pathologic prognostic criteria capable to predict the clinical evolution of a tumour lesion in human patient.

Enabled/vasodilator-stimulated phosphoprotein (Ena/VASP) are key regulatory molecules controlling cell shape, movement and in particular, actin organization. These proteins target the F-actin network and play an important role in cell migration in a number of cell types and organisms.

Ena/VASP proteins are characterized by a highly conserved N-ter EVH1 domain mediating intracellular localization, a central proline rich domain interacting with the G-actin binding protein profillin, SH3 and WW domains of signalling proteins and a C-Terminal EVH2 domain by which the Ena/VASP proteins tetramerize which also possess the functional F-actin binding domain.

Ena/VASP proteins are involved in actin based movement of cells such as fibroblasts (Bear J E et al. 2002) as well as in cell adhesion (Scott J A, et al. 2006).

Ena/VASP proteins can regulate distinct modes of actin organization at cadherin-adhesive contacts and a fine regulation of their expression is necessary for a correct actin network.

Mena is a member of Ena/VASP family which includes Mena, VASP and Evl, all key regulators of actin dynamics (Krause M, et al. 2003). The analysis of the antibody repertoire specific for the molecules expressed by her autologous tumor of a long surviving breast cancer patient have allowed the isolation of the human ortholog of Mena (hMena) as a tumor antigen stimulating an antibody response in cancer patient and not in healthy donors (Di Modugno et al 2004).

Both in human (Urbanelli L et al. 2006) and in murine models (Gertler F et al. 1996), various Mena splice variants have been described and sequenced and some have been associated with particular tissue expression pattern. In mouse a neuronal (N-Mena) form has been described which possess a longer exon 6 that at protein level includes a larger pro-rich region (Gertler F et al. 1996), whereas a splice variant deriving isoform, lacking the pro-rich region has been reported as spleen specific (Tani K et al. 2003).

Mena is up regulated in mouse and rat invasive breast cancer cells (Wang et al. 2004) and overexpressed in human breast cancer tissues where it represents an early marker of breast cancerogenesis (Di Modugno et al. 2006).

The approach of in vivo invasion assay has recently allowed the identification of invasive specific splice variants in murine and rat tumour cells (Goswami S et al. 2009; Philippar et al 2008).

In humans the molecular cloning of hMena and of a splice variant hMena11a from a luminal breast cancer cell line has previously been reported[u1]. This hMena+11a isoform includes an additional 21.aa peptide in the EVH2 domain of the protein, is phosphorylated following EGF and NRG1 treatment and characterizes the epithelial phenotype of breast cancer cell lines (Di Modugno F et al. 2007).

hMena11a isoform expression characterizes pancreatic cancer cell lines showing the epithelial marker E-Cadherin expression, EGFR dependency and sensibility to Erlotinib treatment (Pino M S et al. 2008; and patent WO2009150494). This isoform expression has been recently reported to be regulated by Epithelial Splicing Regulatory Proteins 1 and 2 (ESRP1 and ESRP2), coordinators of an epithelial cell-type-specific splicing program (Warzecha C C et al. 2009).

It has been reported, in a murine and rat model, that invasive tumor cells express higher levels of Mena mRNA containing the +++ exon, but lack the hMena11a isoform, with respect to the non-invasive tumor cells, but the two isoforms are not alternatively expressed (Goswami et al., 2008). Given the above, it is clear that it would be useful to further clarify the molecular pathway underlying the phenotypic changes that define early markers of cancerogenesis and progression of the neoplastic lesion in human in order to identify markers allowing an early and reliable prediction of the behaviour of a neoplastic lesion or even of a pre neoplastic lesion. Such markers would also allow the physician to identify the most appropriate therapeutic approach. In fact, the possibility of predicting in a patient, at early stages of the pre neoplastic or neoplastic lesion, the clinical evolution thereof, may facilitate the design of the most suitable and effective therapeutic approach.

SUMMARY OF THE INVENTION

The inventors of the present application have found a new hMena splicing variant, here called hMena Δv6 (SEQ ID NO: 1), which lacks exon 6 with respect to the hMena known protein. The mere sequence of the new isoform, without any further indication, has been published by the authors on GenBank, Accession n. EU255274 entry. hMenaΔv6 cDNA encodes a protein of 533aa that lacks an internal peptide of 37aa located between the LERER and the Proline-rich region of hMena (FIG. 1). The absence of this peptide get closer two crucial regions, the LERER domain and PKA Ser phosphorylation site (Ser 236 in mice) with the pro-rich domain The inventors have found that the cells showing a migratory ability such as normal fibroblasts and mesenchymal invasive tumor cells express the new isoform variant of hMena, namely hMenaΔv6 or Δv6 isoform of hMena in the present description. The present description provides for the first time the use for diagnostic and medical purposes of said new variant, wherein said expression of said variant is analysed in combination with the hMena11a expression.

In particular, the experiments carried out by the inventors showed that hMenaΔv6 expression together with hMena11a lack of expression are associated to migratory and invasive ability of cells and that hMena Δv6 is alternatively expressed with respect to the hMena11 form, i.e. cells expressing hMenaΔv6 do not express hMena11a and vice versa. Moreover, in early non-small-cell lung cancer (NSCLC) hMena11a expression, related to the expression hMenaΔv6 represents a powerful prognostic factor and usefully complements clinical parameters to accurately predict individual patient risk.

Accordingly, an object of the description is a method for predicting the proliferative or invasive behaviour of a pre neoplastic lesion or of a neoplastic lesion comprising the step of
  detecting in vitro or in vivo the expression of hMena11a and hMenaΔv6 splicing variants of hMena in a biological sample comprising cells of said lesion
  wherein detecting the expression of hMena11a and not of hMenaΔv6 indicates a proliferative behaviour, whereas detecting the expression of hMenaΔv6 and not of hMena11a indicates an invasive behaviour.

Object of the present invention is also a method for predicting the proliferative or invasive behaviour of a pre neoplastic lesion or of a neoplastic lesion comprising the step of
  detecting in vitro or in vivo the presence of antibodies specific for hMena11a and antibodies specific for hMenaΔv6 splicing variants of hMena in a body fluid sample
  wherein detecting the presence of antibodies specific for hMena11a and not of hMenaΔv6 indicates a proliferative behaviour, whereas detecting the presence of antibodies specific for hMenaΔv6 and not of hMena11a indicates an invasive behaviour.

A further object of the present description is a kit for predicting the proliferative or invasive behaviour of a pre neoplastic or neoplastic lesion comprising reagents for detecting the expression of hMena11a and hMenaΔv6 splicing variants in a biological sample of said pre neoplastic or neoplastic lesion.

Other objects of the invention are:
  a nucleotide sequence as set forth in SEQ ID NO: 1 coding for the Δv6 isoform of hMena or fragments thereof said fragments comprising nucleotides from 797 to 807 of SEQ ID NO: 1 (specific for the Δv6 isoform of hMena) or the complementary sequence of SEQ ID NO: 1 or of said fragments;
  the sequences and/or fragments above for use as a diagnostic tool;
  an amino acid sequence as set forth in SEQ ID NO: 2 coding for the Δv6 isoform of hMena or fragments thereof comprising the amino acids from 267 to 270 (specific for the Δv6 isoform of hMena);
  said sequences and/or fragments for use as diagnostic tool;
  a polyclonal or monoclonal antibody or fragments thereof specifically binding a protein having SEQ ID NO: 2 or a fragment thereof specific for the Δv6 isoform of hMena or binding a peptide having SEQ ID NO: 3 (hence still specific for the Δv6 isoform of hMena);
  the polyclonal or monoclonal antibody or fragments thereof specifically binding a protein having SEQ ID NO: 2 or a fragment thereof specific for the Δv6 isoform of hMena or a peptide having SEQ ID NO: 3 as a medicament;
  a siRNA specific for SEQ ID NO: 1 or a fragment thereof comprising nucleotides from 797 to 807 of SEQ ID NO: 1 as a medicament;
  the polyclonal or monoclonal antibody or fragments thereof specifically binding a protein having SEQ ID NO: 2 or a fragment thereof specific for the Δv6 isoform of hMena or a peptide having SEQ ID NO: 3 for use in a treatment for inhibiting of the invasiveness of a pre neoplastic or neoplastic lesion or cells thereof;
  the siRNA specific for SEQ ID NO: 1 or a fragment thereof comprising nucleotides from 797 to 807 of SEQ ID NO: 1 for use in a treatment for inhibiting of the invasiveness of a pre neoplastic or neoplastic lesion or cells thereof;
  a method for the inhibition of the invasive behaviour of a pre neoplastic or neoplastic lesion or cells thereof comprising the step of inhibiting the expression or the functionality and/or the oligomerisation of hMena Δv6;
  a pharmaceutical composition comprising at least one inhibitor of hMena Δv6 expression or functionality and/or oligomerisation and at least a pharmaceutically acceptable carrier and/or excipient;
  a method for the screening of a candidate compound that inhibits the invasive behaviour of a pre neoplastic or neoplastic lesion or cells thereof comprising the step of contacting the compound with a cell line or tissue culture expressing the hMena Δv6 isoform of hMena, wherein the reduction in the expression of said isoform is indicative that the compound is a candidate compound for inhibiting the invasive behaviour of a pre neoplastic or neoplastic lesion or cells thereof.

hMena Δv6 isoform interacts with the other hMena isoforms and with other members of Ena/VASP family to form functional tetramers which regulate actin cytoskeleton dynamics Inhibition of hMenaΔv6 inclusion into the tetramers or exogeneous inclusion of hMena11a may change the function of the tetramer in terms of actin network and ultimately in the ability of the cell to invade.

Since, hMena has been isolated as a tumor antigen able to induce an antibody response in neoplastic patients and not in healthy donors (Di Modugno et al 2004), the present invention also provide a method for the detection of antibodies specific for each hMena isoform from the sera of preneoplastic or neoplastic cancer patients, using recombinant proteins or peptides peculiar of each hMena isoforms new and/or available in the art and conventional ELISA tests.

The findings disclosed in the present application not only allow the prediction of the proliferative or invasive behaviour of a pre neoplastic or of a neoplastic lesion, hence offering the advantage of defining an efficacious medical treatment since the early stage of the tumour development, but also prove the therapeutic effects of inhibitors or blockers of the hMena Δv6 isoform, wherein the inhibition of either the expression or of the activity or of the oligomerisation of the hMena Δv6 isoform directly inhibits the invasive behaviour of cells and tissues expressing said isoform.

A. Diagrammatic representation of hMenaΔv6 protein isoform. Protein domains are indicated with the enumeration of relative amino acids. Sequence and position of peptide V6, absent in hMenaΔv6 isoform is indicated.

B. In vitro translated hMena and hMenaΔv6 analyzed by Western blot analysis using the CKLK1 Ab (10 μg/ml). Protein extracts (30 μg) of MDAMB231 (used to obtain hMenaΔv6 and hMena cDNAs) breast cancer cell line were also tested by Western blot to identify the corresponding in vitro translated protein bands in whole cell lysates.

C. RT-PCR performed with primers (MTC1f and MTC4r) flanking the region of alternative splicing on MDAMB231; BT549; MCF7 and SBT RNA. PCR experiment was also done on the pcDNA3.1 vectors containing the three hMena variants. PCR products were analyzed by agarose gel electrophoresis and ethidium bromide staining.

Figure 2:
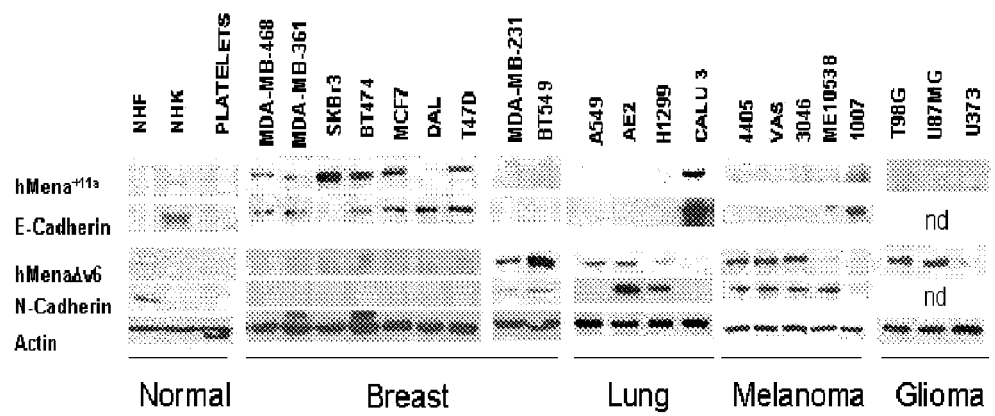

FIG. 2. hMena11a and hMenaΔv6 are alternatively expressed and correlate with an epithelial or mesenchymal and phenotype respectively.

Western Blot analysis of lysates of normal keratynocytes (NHK), fibroblasts (NHF) and platelets and of tumor cell lines with hMena isoform specific antibodies, anti E-Cadherin and N-Cadherin antibodies, indicating that normal human keratinocytes expressed hMena11a and the epithelial marker E-Cadherin whereas fibroblast expressing the mesenchymal marker N-cadherin are negative for hMena11a and expressed hMenaΔv6. Normal cells showed a very low level of hMena expression and platelets were negative as described. All the breast and lung cancer cell lines expressing hMena11a show a concomitant expression of E-Cadherin. Conversely, the lack of hMena11a expression is always correlated with the absence of E-Cadherin the expression of the mesenchymal markers as N-Cadherin and the expression of hMenaΔv6 isoform.

Figure 3:
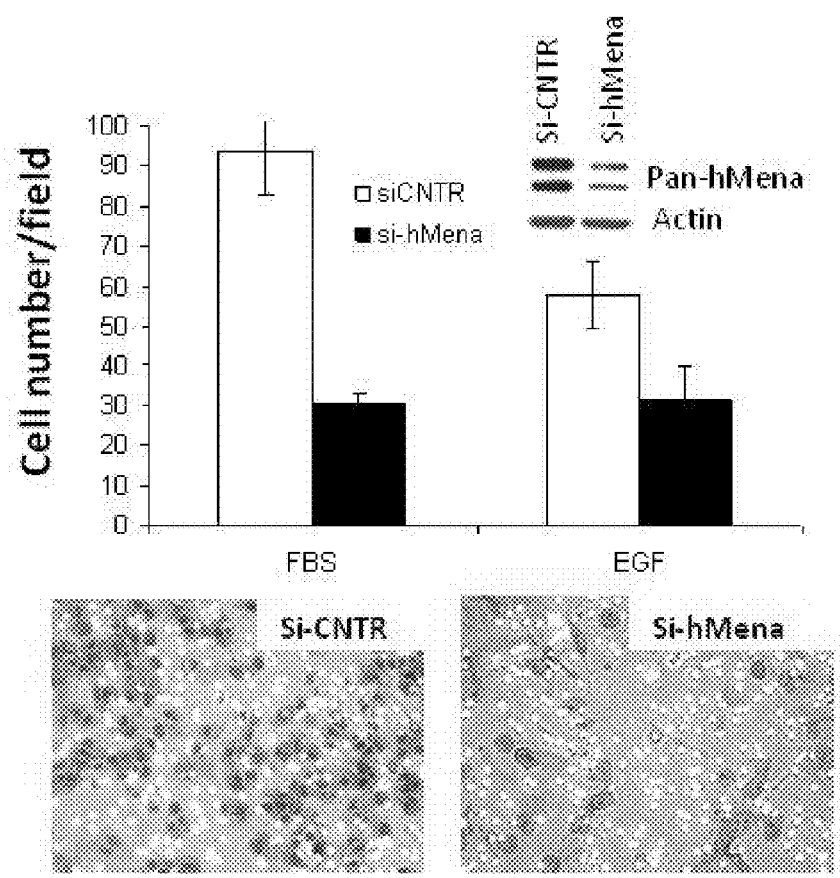

FIG. 3. hMenaΔv6 is required for invasion of breast cancer cell lines.

Matrigel invasion assay performed on BT549 cells transfected with the indicated siRNA. The ability of invasion has been measured during the last 24 h of transfection by the use of Matrigel coated transwell filters (BD Biosciences) toward a gradient of EGF or serum. The assay was repeated three times each time performed in triplicate. Histograms represent the mean of invading cells counted in ten different fields±SD. Representative images are shown. Inset: Western blot analysis of lysates of BT549 cells collected following 72 h of siRNA transfection. The experiment reported in this figure demonstrates that the knock down of hMena isoforms in invasive breast tumor cells expressing hMena/hMenaDv6 significantly reduces the invasive behaviour of the cells.

Figure 4:
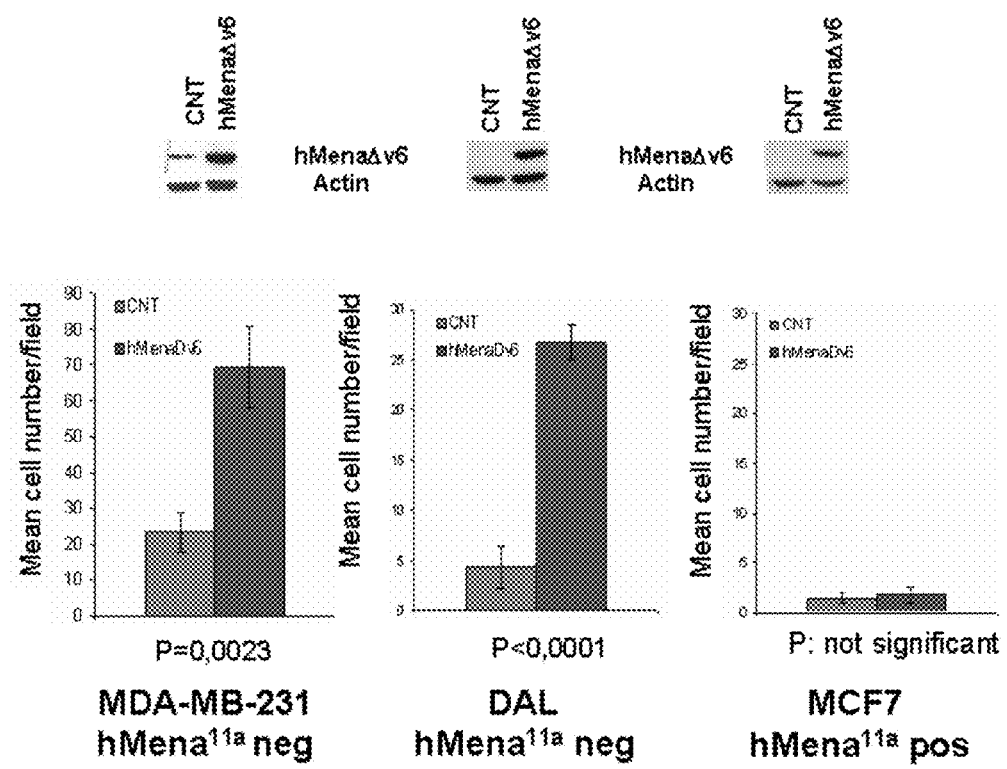

FIG. 4. hMenaΔv6 transfection increases the invasive ability of breast tumor cells only in the absence of hMena11a.

Matrigel invasion assay performed on MDA-MB-231 (hMena11a negative, hMena/hMenaΔv6 positive), DAL (expressing an undetectable levels of hMena isoforms) and MCF7 (hMena/hMena11a positive, hMenaΔv6 negative) cells stably transfected with the empty vector or hMenaΔv6 toward serum. The ability of invasion has been measured by the use of Matrigel coated transwell filters (BD Biosciences) toward a gradient of serum. Results shown indicate that hMenaΔv6 overexpression increases the invasive behaviour of the hMena11a negative MDAMB231 and DAL cells, but has no effect on hMena11a positive MCF7 cells. The assay was repeated three times each time performed in triplicate. Histograms represent the mean of invading cells counted in ten different fields±SD. Western blot analysis of lysates of transfected cells indicating the efficiency of hMenaDv6 transfection are shown on the top of the histograms.

Figure 5:
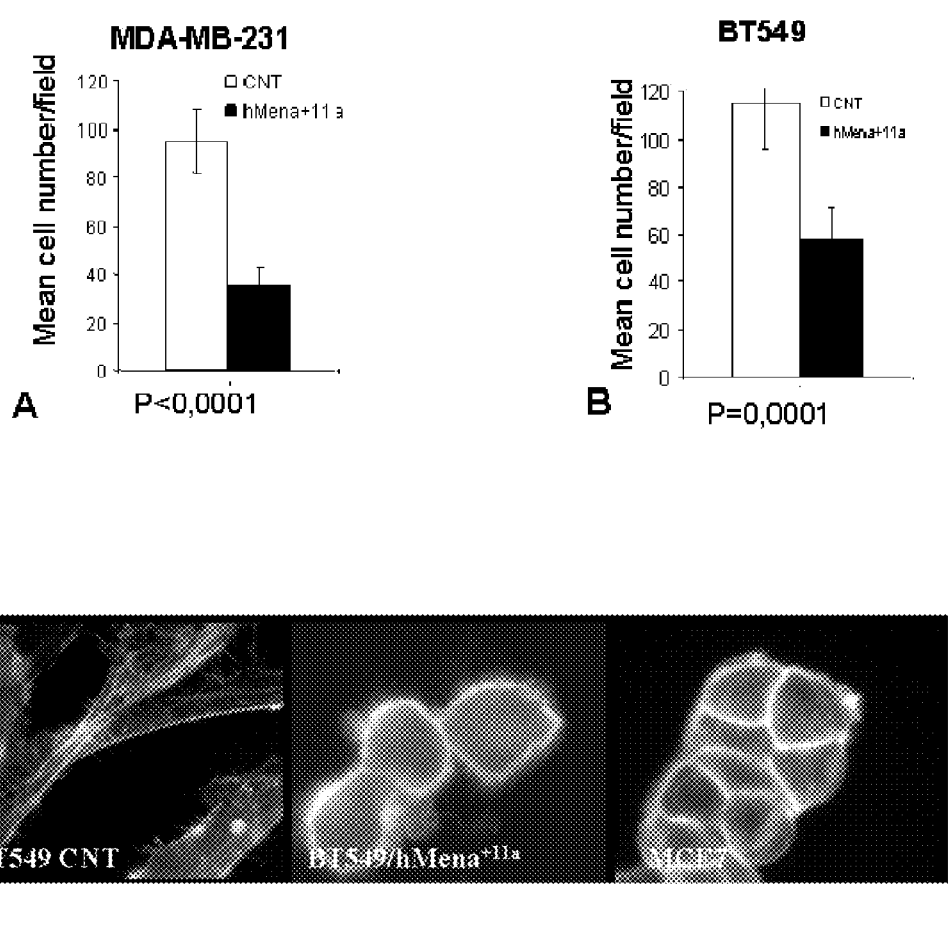

FIG. 5. hMena 11a transfection inhibits invasion and directional migration of breast cancer cell lines and determine a dramatic reorganization of actin cytoskeleton.

A. Matrigel invasion assays of MDA-MB-231 (hMena11a negative hMena/hMenaΔv6 positive) stably transfected with empty vector or hMena11a. The ability of invasion has been measured by the use of Matrigel coated transwell filters (BD Biosciences) toward a gradient of serum. The assay was repeated three times each time performed in triplicate. P value and standard deviations are indicated. Western blot analyses of lysates of transfected cells is shown on the top of the histograms.

B. Matrigel invasion assays of BT549 cells (hMena11a negative hMena/hMenaΔv6 positive) stably transfected with empty vector or hMena11a performed as described in panel A. Western blot analyses of lysates of transfected cells is shown on the top of the histograms.

C. Immunofluorescence analysis of BT549 cells transfected with the empty vector or with hMena11a and of MCF7 cells with phalloidin (red). Cells were imaged using immunofluorescence microscopy DMIRE2 (Leica Microsystems) and processed using FW4000 Software. Magnification: 63×.

Figure 6:
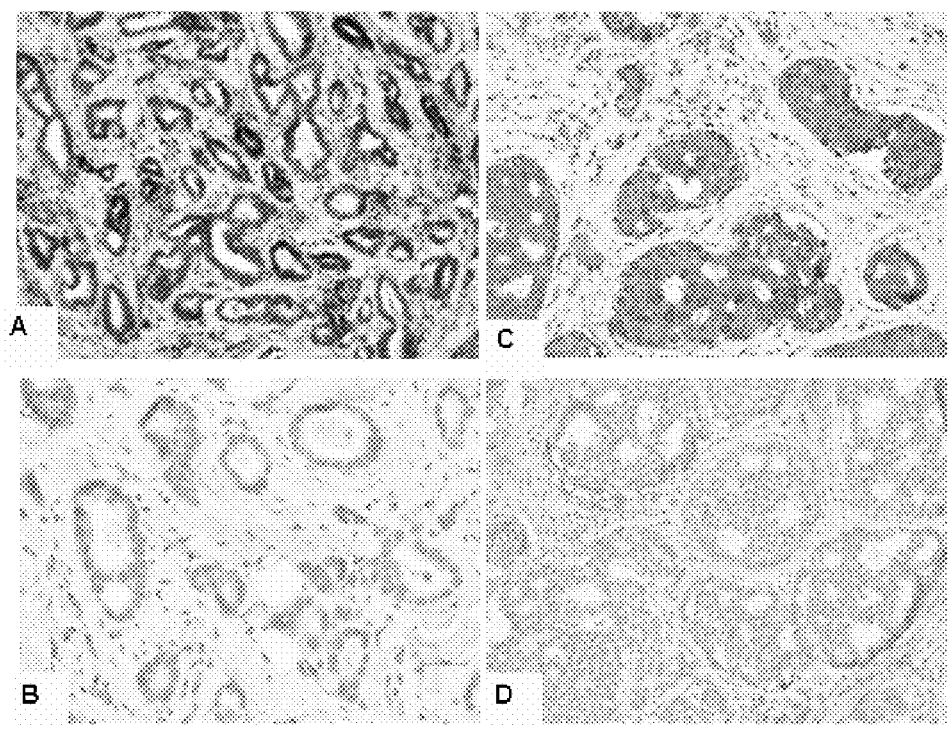

FIG. 6. Characterization of hMena11a and hMenaΔv6 specific antibodies for immunohistochemical analysis. Pretreatment with specific peptide abolishes immunohistochemical reactivity of hMena isoforms' antibodies.

A-B. Consecutive sections of a breast cancer tissue expressing hMena11a decorated with anti-hMena11a antibody pretreated with irrelevant peptide (Δv6) (A) or with the specific 11a peptide (B).

C-D. Consecutive sections of a breast cancer tissue expressing hMena Δv6 decorated with anti-hMenaΔv6antibody pretreated with irrelevant peptide (11a) (C) or with the specific Δv6 peptide (D).

Figure 7:
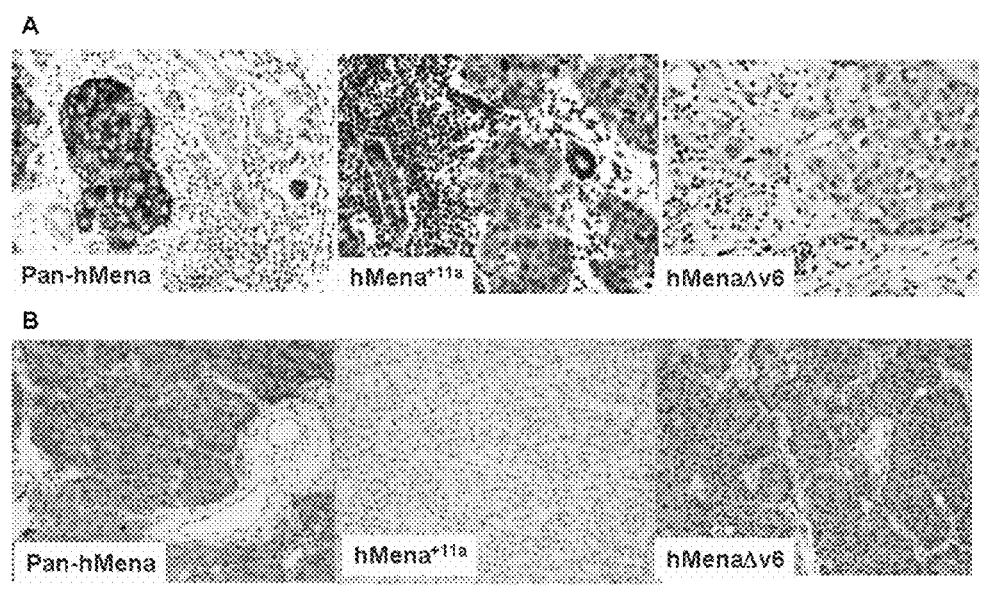

FIG. 7. Representative immunohistochemical analysis of consecutive sections of two invasive breast tumor tissues.

The case reported in panel A is positive for the staining with pan-hMena and expresses hMena11a, but is negative for hMenaDv6. The case reported in panel B is positive for the staining with pan-hMena and expresses hMenaDv6, but is negative for hMena11a.

The tumour is an epithelial tumour.

According to an embodiment of the invention the method for detecting both said splicing variants is carried out by detection of the corresponding protein by immunohistochemistry.

In a still alternative embodiment of the invention the detection of hMena splicing variants is carried out by detecting transcription products comprising SEQ ID NO: 8 or fragments thereof and transcription products comprising the junction between exon 5 and 7 of hMena.

DETAILED DESCRIPTION OF THE INVENTION

The present description discloses a method for predicting the proliferative or invasive behaviour of a pre neoplastic lesion or of a neoplastic lesion comprising the step of
detecting in vitro or in vivo the expression of hMena11a and hMenaΔv6 splicing variants of hMena in a biological sample comprising cells of said lesion wherein detecting the expression of hMena11a and not of hMenaΔv6 indicates a proliferative behaviour, whereas detecting the expression of hMenaΔv6 and not of hMena11a indicates an invasive behaviour.

Human Mena11a isoform of hMena (herein also defined as hMena11a) (F. Di Modugno et al. 2007) is a splicing variant of hMena resulting in the corresponding hMena11a protein isoform. This splicing variant contains the additional exon 11a of 63 nucleotides, corresponding to an additional peptide of 21 amino acids in the EVH2 domain characterizing the isoform. The hMena11a has the nucleotide sequence of SEQ ID NO: 6 coding for the amino acid sequence of SEQ ID NO: 7, whereas the exon 11a has the nucleotide sequence of SEQ ID NO: 8 that codes for a peptide of SEQ ID NO: 9.

The present inventors have identified a new hMena splicing variant in a human breast cancer cell line with a mesenchymal phenotype. Said splicing variant (GEN BANK NO EU255274) has been called the human MenaΔv6 and is characterized, compared to hMena, by the lack of the internal exon 6 of 111 nucleotides (FIG. 1A). The hMenaΔv6 has the nucleotide sequence of SEQ ID NO: 1 coding for the protein isoform Δv6 of SEQ ID NO: 2 and lacks an internal peptide of 37 aa located between the LERER domain and the Pro-rich region of hMena.

The absence of this peptide puts two crucial regions, the LERER domain and PKA Ser phosphorylation site (Ser 236 in mice) with the pro-rich domain close to each other in the Δv6 protein.

Exon 6 spans from nucleotide 803 to nucleotide 813 included of SEQ ID NO: 6 coding hMena11a. The sequence coding for hMena 11a is identical to hMena sequence up to nucleotide 1540.

In the present description the expression "invasive behaviour of a pre neoplastic or of a neoplastic lesion" refers to pre neoplastic or neoplastic lesions comprising cells that tend to leave the primary tumor and to acquire migratory and invasive capabilities, spread and migrate form an original site to one or more sites elsewhere in the body.

The expression pre neoplastic lesion (i.e. pre cancer lesion) refers to lesions preceding the formation of a malignant neoplasm, i.e. a lesion from which a malignant tumour is presumed to develop in a significant number of instances and that may or may not be recognizable clinically or by microscopic changes in the affected tissue, i.e. a condition that tends to become malignant but does not necessarily do so.

The expression neoplastic lesion refers to a lesion pertaining to a neoplasm or a neoplasia, i.e. an abnormal growth of cells, which may lead to a neoplasm, or tumor.

The experiments carried out by the inventors showed that said two splicing variants, namely hMena11a and hMena Δv6, are mainly expressed in an alternative manner and characterize two different cellular phenotypes. In particular, hMena11a is expressed in the cells showing an epithelial phenotype, i.e. cells expressing the major component of the epithelial adherent junctions E-Cadherin, whereas hMenaΔv6 is only present in cells showing a migratory ability, such as fibroblasts and tumor cells, lacking E-Cadherin and hMena11a expression but expressing the mesenchymal marker N-Cadherin and or vimentin. As shown in FIG. 2A both in normal cells, such as keratynocytes and fibroblasts, and in human cancer cell lines the lack of hMena11a expression is always correlated with the presence of hMena Δv6 isoform expression and mesenchymal markers expression as N-Cadherin.

Conversely, the lack of hMenaΔv6 expression is always correlated with the presence of hMena11a and the expression of markers such as E-Cadherin.

The results obtained by the authors allow demonstrating that the detection of hMena11a expression and not of hMenaΔv6 expression indicates a proliferative anti invasive behaviour, whereas the detection of hMenaΔv6 expression and not of hMena11a expression indicates an invasive behaviour of a pre neoplastic or neoplastic lesion in a human patient.

For the purpose of the invention the neoplastic lesion can be a tumour originating from any tissue of the body;

In a particular embodiment of the invention the lesion can be a tumour selected from the group comprising: pancreatic, breast, colorectal, gastric, ovarian, lung, prostate, urothelial, head and neck, esophageal, skin tumour including melanoma.

Biological sample comprising lesion cells within the meaning of the invention means a specimen of a pre neoplastic or neoplastic lesion tissue, pre neoplastic or neoplastic lesion cells or blood free-circulating neoplastic cells collected from samples of body fluids such as blood, serum, lymphatic liquid. The said biological samples may be obtained form subjects by standard techniques, such as biopsy, surgery or aspiration, well known to the person skilled in the art.

The method of the invention can also be carried out on blood samples of patients, in order to detect the presence of circulating tumour cells (CTC) i.e. cells of the neoplastic lesion that are freely circulating in blood. Said cells, in fact, can be detected in the peripheral blood of patients with a variety of solid cancers. Because of their very low frequency, these tumour cells are not easily detected using conventional cytology methods. In the past decade, numerous groups have attempted to detect CTC of solid malignancies using the highly sensitive reverse transcriptase polymerase chain reaction, which has been shown to be superior to conventional techniques. However, the biological significance of CTC and the therapeutic relevance of their detection are still debated. The method herein described, allows identifying CTC of tumours that are proliferating or invasive thus enabling also researchers to further investigate the potential of identification and molecular characterization of the subset of CTC responsible for metastasis development. The prognostic value of CTC would provide clinicians with a unique tool for better stratification of patients' risk and provide basic researchers with a new target for the development of novel therapeutic approaches. The method of the invention advantageously enables the detection of a large group of CTC of different tumours.

The detection of said two splicing variants may be carried out at different stages of the expression process. In other words it is possible to detect hMena variants either by detecting the expressed protein isoforms or by detecting the transcription products, namely the spliced transcript mRNA of hMena variants or alternatively the cDNA obtained by reverse transcription of said mRNA. Therefore, said detection can be carried out by detecting directly or indirectly either nucleotide sequences or amino acid sequences of hMena variants. In any case the hMena11a and hMenaΔv6 expression shall be normalized with respect to other proteins or transcription products whose expression does not change in proliferative or invasive/metastatic tumors. Examples of such controls include hMena isoform (88 kDa) and VASP.

Methods suitable for the detection are either qualitative or quantitative ones.

In one embodiment of the invention the detection of one or both said splicing variants is carried out identifying the protein variants by immunohistochemistry or immunocytochemistry.

The immunohistochemistry or immunocytochemistry allows the localization of a target antigen in cells, tissues etc. by using an antibody and exploiting the specific antigen-antibody interaction. Therefore some suitable methods for the detection of hMena variants by direct cellular analysis with immunochemistry techniques are, for illustrative purposes, western blot, immunofluorescence techniques etc.

The immunohistochemistry is carried out directly on a tissue sample and as well known by the skilled person; all the stages of this technique are described in detail in most laboratory manuals.

The method according to the present invention may be carried out by using a polyclonal or a monoclonal antibody or an immunologically active fragment thereof specific for the isoform 11a of the hMena protein for hMena11a detection and a polyclonal or a monoclonal antibody or an immunologically active fragment thereof specific for the isoform Δv6 of the hMena protein for hMenaΔv6 detection.

The polyclonal or monoclonal antibodies can be obtained by the skilled person following standard techniques, by way of example, by immunising rabbits, or mice, or other suitable animals so to obtain antibodies specific for the desired variants. For the preparation of anti hMena11a antibodies, the animals can be immunised, by way of example, with an immunogenic peptide specific for hMena 11a, e.g. a peptide comprising or comprised in exon 11a of SEQ ID NO: 9 or an antigenic portion of hMena11a SEQ ID NO: 7 specific for hMena 11a or by conformational epitopes specific for the desired isoform. For the preparation of anti hMena 4v6 antibodies, the animals can be immunised, by way of example, with an immunogenic peptide specific for hMena 4v6 e.g. with a peptide encoded by a fragment of SEQ ID NO: 1 comprising nucleotides from 797 to 807 or with an antigenic portion of SEQ ID NO: 2 specific for hMena4v6 or with any suitable immunopeptide specific for hMena4v6 as the peptide of SEQ ID NO: 3 or by conformational epitopes specific for the desired isoform. In an embodiment of the present description, said antibody or fragment thereof specific for the hMena11a isoform is specific for an epitope comprised in or consisting of SEQ ID NO: 9 and said antibody or fragment thereof specific for the hMena4v6 isoform is specific for an epitope comprised in or consisting of SEQ ID NO: 2 or SEQ ID NO: 3.

An effective polyclonal antibody for carrying out the methods herein described can be obtained by immunising rabbits with the antigen conjugated with a protein carrier such as for example KLH or BSA.

The immune sera thus obtained can be purified by affinity chromatography for example on Sepharose resin CnBr conjugated with the immunogenic peptide. The immunogenic peptide used in affinity chromatography for purifying anti-hMena4v6 may be, by way of example, the peptide of SEQ ID NO: 4. The anti-hMena11a or the hMena4v6 thus obtained will specifically recognise the hMena11a or the hMena4v6 isoform without cross reacting with other hMena isoforms.

Suitable monoclonal antibodies can be manufactured by ablating the spleen of animals immunised with the above described immunogens and by fusing the spleen cells with mieloma cells in order to form an hybridome that, once cultured, will produce the monoclonal antibody. The antibody can be an IgA, IgD, IgE, IgG or IgM. The IgA antibody can be an IgA1 or IgA2, the IgG can be an IgG1, IgG2, IgG2a, IgG2b, IgG3 or IgG4. Also a combination of antibodies subtypes can be used. The antibody can be a human, mouse, goat or rabbit antibody. The antibodies can be humanised by using standard techniques of recombinant DNA known to the skilled person.

As used herein, the term antibody encompasses whole antibodies and fragment thereof wherein the fragment specifically binds to one of the said hMena protein isoforms.

The fragment according to the present description can be, without being limited to it, an F(ab')2 fragment, a Fab' fragment or single chained antibodies.

Aptamers may also be used in order to detect the hMena protein isoforms. Aptamers are single strand oligonucleotides that bind to a particular target molecule, such as a protein. Thus, aptamers are functionally similar to antibodies. Aptamers that bind a target molecule can be selected using, for example, the SELEX process or the like.

The reagent binding the hMena isoforms (deriving from the hMena RNA splicing variants) can be complexed with a detectable marker or alternatively be detectable itself by a second labelled reagent such as a second antibody. The labelling can be carried out through many know techniques including but not limited to, peroxydase, chemoluminescence, radioactive markers. The marker can be a non radioactive or a fluorescent marker such as biotin, fluorescein (FITC), acridine, carboxy-X-rhodamine and others known to the skilled person, that can be detected by means if fluorescence techniques or other image analysis techniques.

Alternatively, the marker can be a radioisotope emitting radiations such as, by way of example $^{35}$S, $^{32}$P, o $^{3}$H. The emitted radioactivity can be detected by means of know standard techniques, such as, by way of example, scintigraphy.

The detection of hMena splice variants can be also carried out at transcriptional level. Thus, it is possible to detect transcription products such as mRNA or the relative cDNA. Protocols to obtain mRNA or cDNA from a sample comprising cells of interest are well known by the skilled person and furthermore they are described in detail in laboratory manuals and in commercially available kits for mRNA extraction and cDNA amplification. The detection of transcription products may be carried out by any suitable method such as northern blot, microarray, PCR, Real-Time PCR, hybridization on solid support etc.

According to the present invention, the detection of one or both said splicing variants is carried out by detecting transcription products comprising SEQ ID NO: 8 or fragments thereof for the detection of the hMena11a variant and transcription products comprising nucleotides from 797 to 807 of SEQ ID NO: 1 for the detection of the hMenaΔv6 variant.

The expression of the hMena11a and hMenaΔv6 splicing variants can be detected by nucleic acids hybridisation analysis using one or more probes hybridising in a specific manner with the mRNA or cDNA of said variants.

In one embodiment of the invention, the detection is carried out by hybridising the mRNA or cDNA obtained from the sample with a labelled oligonucleotide comprising SEQ ID NO: 8 and/or its complementary sequence or a fragment thereof and with another labelled oligonucleotide comprising nucleotides from 797 to 807 of SEQ ID NO: 1 or and/or of their complementary nucleotides in the sequence complementary to SEQ ID NO: 1.

The oligonucleotide may be DNA or RNA and may be prepared by a variety of techniques known to those skilled in the art, including, without limitation, restriction enzyme digestion of hMena variants, automated synthesis of oligonucleotides. It is clear that the skilled person, knowing the nucleotide sequences (SEQ ID NO: 6 of hMena11a and the sequence of exon 11a SEQ ID NO: 8 and SEQ ID NO: 1 of hMena4v6 and the exact sequence of the exon 5 and exon 7 junction comprised between nucleotides 797 to 807 of SEQ ID NO: 1) will be capable, without use of inventive skill, to design probes suitable for carrying out the hybridization method.

The oligonucleotides for hybridisation may be vary in length form about 8 nucleotides to the entire sequence SEQ ID NO: 8 for hMena 11a detection and may vary from nucleotides 797 to 807 (plus or minus one nucleotide per side) to a fragment of about 10-500 nucleotides of SEQ ID NO: 1 comprising nucleotides 797-807 according to the specific hybridization technique used.

In general, the length of the probe can be a length suitable for hybridisation. Suitable length can be between, by way of example, 500 and 10 nucleotides, such as about 400, 300, 200, 150, 100, 60, 50, 40, 30, 20, 10 nucleotides, as known to the skilled person.

The hybridization may be carried out by different methods such as northern blot (for RNA detection), southern blot (for cDNA detection), hybridization on a solid phase, i.e. on a solid support such as microtiter, microarray chip and the like. The detection is due to a luminous signal in correspondence to the hybridization between the target molecules or fragments thereof and the corresponding probe. As well known to the skilled person it is possible to label either the probe or the target molecules according to the particular method used.

So, by way of example, the detection of one of both hMena variants, when carrying out hybridization on solid support, is due to the luminous signal (emitted by a fluorophore) in correspondence to the hybridization between the target molecule labelled and the corresponding probe bound on the support. Each variant will be labelled with a different fluorophore in order to enable direct identification of the variant expressed.

Conversely, the oligonucleotide probes are labelled in southern and northern blot techniques.

Protocols suitable for carrying out any of these hybridization techniques are described in details in laboratory manuals and the skilled person will be capable, without use of inventive skill, to carry out the detection of hMena variants according to this embodiment of the invention.

In another embodiment of the invention, said detection is carried out by PCR by amplifying the mRNA or cDNA obtained from the sample with a primer pair amplifying SEQ ID NO: 8 or a fragment thereof and with another primer pair amplifying a fragment of SEQ ID NO: 1 comprising nucleotides from 797 to 807 of SEQ ID NO: 1.

Even in this case, the skilled person, knowing the nucleotide sequences (SEQ ID NO: 6, SEQ ID NO: 8, SEQ ID NO: 1, and sequence from 797 to 807 of SEQ ID NO: 1) will be capable to design primers suitable for carrying out the amplification. Further the primers may be labelled with detectable markers such as fluorophores and others known to the skilled person in order to identify the specific amplicons, by way of example, after an RT-PCR. The detection of amplicons related to more than one variant, obtained by PCR carried out with unlabelled primers, may be possible by designing, as well known to the skilled person, primers capable of amplifying sequences with a different number of nucleotides. Thus, the obtained amplicons may be detected by their different migration pattern on electrophoresis gel.

In Real-time PCR the detection of the target sequence is based on to the study of melting curves so, indifferently from the method used for the revelation, the obtained amplicons may be of the same length.

The present description also provides a method for predicting the proliferative or invasive behaviour of a pre neoplastic lesion or of a neoplastic lesion comprising the step of detecting in vitro or in vivo the presence of antibodies specific for hMena11a and antibodies specific for hMenaΔv6 isoforms of hMena in a body fluid sample. As used herein, the term antibody encompasses whole antibodies and fragment thereof specifically capable of binding to one of the said hMena protein isoforms or fragments thereof. For illustrative purpose, detectable antibodies useful for carrying out the method above described, are detectable antibodies capable of recognizing and specifically binding SEQ ID NO: 2 or fragments thereof, SEQ ID NO: 9, SEQ ID NO: 7 or fragments thereof or SEQ ID NO: 10.

Detecting the presence of antibodies specific for hMena11a and not of hMenaΔv6 isoforms in a body fluid sample indicates a proliferative behaviour of a pre neoplastic lesion or of a neoplastic lesion, whereas detecting the presence of antibodies specific for hMenaΔv6 and not of hMena11a indicates an invasive behaviour of said lesion.

In one embodiment said lesion is a neoplastic lesion and said lesion is selected from the group comprising: pancreatic, breast, colorectal, gastric, ovarian, lung, prostate, urothelial, head and neck, esophageal and skin tumours including melanoma.

The antibodies specific for said hMena isoforms can be detectable in a body fluid sample. Body fluids suitable for carrying out the method above comprise: blood, serum, breast milk, peritoneal fluid, pleural fluid, pericardial fluid, lymph.

As well known by the skilled person, techniques for detecting antibodies in a fluid are described in detail in most laboratory manuals and therefore, herein they don't need any other technical detail. Anyway, by way of example, a suitable technique for carrying out said method is the ELISA assay.

The present description also discloses a kit for carrying out the method of the invention. The kit herein described allows predicting the proliferative or invasive behaviour of a pre neoplastic or neoplastic lesion by detecting the expression of hMena11a and hMenaΔv6 isoforms in a biological sample of said pre neoplastic or neoplastic lesion or cells thereof.

The kit of the present description will comprise reagents suitable for the detection of both variants and optionally positive and negative controls.

In an embodiment, the kit will comprise a polyclonal or a monoclonal antibody or an immunologically active fragment thereof specific for the isoform 11a of the hMena protein and a polyclonal or a monoclonal antibody or an immunologically active fragment thereof specific for the isoform Δv6 of the hMena protein.

The antibody or antibodies of the kit can be aliquoted in one or more vials, in master solutions or ready-to-use solutions, they can be labelled in any of the above described manners. Depending on the labelling selected, the kit of the invention can further comprise the reagents suitable for the detection of said antibody. All the labelling options are well-known in the art and the detection protocols and reagents are also well known to the skilled person.

In one embodiment of the invention, the antibody or fragment thereof specific for the hMena11a isoform is specific for an epitope comprised in SEQ ID NO: 9 or any other epitope specific for hMena11a isoform, and wherein said antibody or fragment thereof specifically binds a protein having SEQ ID NO: 2 or any other epitope specific for the hMenaΔv6 isoform or a peptide having SEQ ID NO: 3

Alternatively, the kit can comprise a labelled oligonucleotide comprising SEQ ID NO: 8 and/or its complementary sequence or a fragment thereof and another labelled oligonucleotide comprising nucleotides from 797 to 807 of SEQ ID NO: 1 or and/or their complementary nucleotides in the sequence complementary to SEQ ID NO: 1.

When due to hybridise on cDNA the probes can be designed in order to hybridise to the sense or the antisense strand, and will comprise a region of at least part of the sequence coding for hMena11a cDNA said region comprising SEQ ID NO: 8 or a region of at least part of the sequence coding for hMenaΔ6 cDNA said region comprising nucleotides from 797 to 807 of SEQ ID NO: 1.

As before, the labelling can be any suitable labelling indicated above. The kit may hence further comprise reagents suitable for the detection of the labelled probe.

Alternatively, the kit can comprise a primer pair amplifying SEQ ID NO: 8 or a fragment thereof and another primer pair amplifying a fragment of SEQ ID NO: 1 comprising nucleotides from 797 to 807 of SEQ ID NO: 1.

The kit may further comprise further reagents suitable for the detection of the expression of hMena11a and hMenaΔv6 splicing variants such as buffers, supports, gels, membranes and others. In other words, the kit of the present invention can comprise any and all reagents necessary for carrying out one or more of the detection methods described above. Reagents, by way of example, may be one o more aliquots of suitable buffers (Tris buffer), dNTPs, Taq polymerase, $MgCl_2$, reverse transcriptase, microarray, microtiter, gels, membranes, specific enzymes etc. The kit of the present invention may be a partial kit which comprises only a part of the necessary reagents or enzymes an in this case the users may provide the remaining components.

The kit may comprise means for carrying out one or more methods described above. For example, the kit may include microtiter, solid support, precasting gels (electrophoresis gel, northern gel, southern gel) etc.

The kit may further comprise positive and/or negative control samples such as ready to use tissue or cell samples expressing hMena 11a or hMena Δv6 fixed or fresh hMena isoform transfected or knock down tumor cells or tumor cell lysates and/or cDNA from cells and or tissues expressing hMena 11a or of hMena Δv6. The samples can be provided for both isoforms or for one of the two isoforms.

The presence of positives and/or negative controls will allow the user to verify the effectiveness of the reagents and the presence of a possible background signal in the detection assay.

The invention also provides a nucleotide sequence as set forth in SEQ ID NO: 1 coding for the Δv6 isoform of hMena or fragments thereof said fragments comprising nucleotides from 797 to 807 of SEQ ID NO: 1 or the complementary sequence of SEQ ID NO: 1 or of said fragments.

These nucleotide sequences may be used as a diagnostic tool, for example, to identify, to determine the nature, the cause, the behaviour (proliferative or invasive behaviour) of a pre neoplastic lesion or of a neoplastic lesion.

Another embodiment of the invention is an amino acid sequence as set forth in SEQ ID NO: 2 coding for the Δv6 isoform of hMena or fragments thereof comprising the amino acids from 267 to 270. These amino acid sequences, as the corresponding nucleotide sequences, may be used as a diagnostic tool or for the preparation of isoform specific antibodies or aptamers.

An embodiment of the present invention is also a polyclonal or monoclonal antibody or fragments thereof specifically binding a protein having SEQ ID NO: 2 or an epitope specific for hMenaΔv6 isoform or a peptide having SEQ ID NO: 3.

Said polyclonal or monoclonal antibody or fragments thereof may be used as a medicament. The expression "as a medicament" means, in present description, that said antibody is capable to modify the functionality or oligomerization of hMena Δv6 protein and then causing an alteration of actin cytoskeleton of the cell both in vivo and in vitro thus inhibiting its invasive behaviour.

The invention still further provides a siRNA specific for SEQ ID NO: 1 or a fragment thereof comprising nucleotides from 797 to 807 of SEQ ID NO: 1 as a medicament.

RNA interference (RNAi) is a process by which double-stranded RNA (dsRNA) is used to silence gene expression. RNAi begins with the cleavage of longer dsRNA into small interfering RNAs (siRNAs) by an RNaseIII-like enzyme, dicer. siRNAs are dsRNAs that are usually about 19 to 28 nucleotides or 20 to 25 nucleotides. A single dsRNA is incorporated into a ribonucleoprotein complex known as RNA-induced silence complex (RISC). RISC uses the antisense strand (or guide strand) of siRNA to identify mRNA molecules that are at least partially complementary to said siRNA strand, and then inhibits their translation. Therefore, the other siRNA strand, known as passenger strand or sense strand, is eliminated from the siRNA as it is partially homologus to the target mRNA.

RISC-mediated cleavege of mRNA having a sequence at least partially complementary to the guide strand leads to decrease in the steady level of that mRNA and of the corresponding protein encoded by this mRNA. Alternatively, RISC can also decrease expression of a protein via translation repression without cleavage of mRNA molecule.

The present invention relates to the use of interfering RNA to inhibit or reduce the expression of hMena, in particular hMenaΔv6 splicing variant by either cleaving or repressing translation of hMenaΔv6 mRNA.

In order to carry out the interference process described above, the skilled person in the art can readily deduce the mRNA sequence of hMena Δv6 from the corresponding DNA sequence of SEQ ID NO: 1. The mRNA sequence is identical to the DNA sense strand sequence with "T" bases replaced with "U" bases. Therefore, the mRNA sequence of hMena is known from SEQ ID NO: 1.

In one embodiment of the invention the siRNA has a sense strand identical to SEQ ID NO: 1 or a fragment thereof comprising nucleotides from 797 to 807 of SEQ ID NO: 1.

Suitable siRNAs for hMena Δv6 can be designed using available design tools such as Ambion o Genscript programs freely available online at: http://www.ambion.com/techlib/misc/siRNA_finder.html   http://www.genscript.com/design_center.html) or can be ordered to specialized commercial suppliers. Techniques for selecting suitable siRNA are provided by Tuschl, T et al. "The siRNA user guide" available on the Rockefeller University web site; and by other web-based design tools at, for example, Invitrogen, Integrated DNA Techologies, Genscript web site.

Designed siRNAs corresponding to the target molecule may be tested by measuring the mRNA levels or corresponding protein levels in the cells treated with said siRNAs, by techniques well known to the skilled person such, for example, western blot, PCR etc.

A siRNA according to the present description for targeting hMena Δv6 mRNA may be, by way of example, sense strand siRNA: UAUCAAGUGCUGGCAUUG UUU (SEQ ID NO: 17); Antisense strand siRNA: ACAAUGCCAGCAC-UUGAU AUU (SEQ ID NO: 18).

For the purpose of the invention herein described the antisense strand of siRNA may have between 80% up to 100% complementary, for example 85%, 90%, 95%, 96%, 97%, 98%, 99% or 100% complementary, to the hMena Δv6 mRNA sequence.

According to present invention single strand interfering RNAs (ssRNA) may be used in order to achieve the inhibition of hMena Δv6 expression. Therefore, embodiments of the present invention are also ssRNAs that specifically hybridise to SEQ ID NO: 1 or a fragment thereof comprising nucleotides from 797 to 807 of SEQ ID NO: 1.

Alternatively, the interference may be carried out by an expression vector having a coding sequence that is transcribed to produce one or more transcriptional products that produce double or single strand siRNA specific for hMena Δv6 in the cells.

Optionally, a hairpin RNA (shRNA) which is processed to a siRNA may be used.

In the meaning of the invention, siRNA includes all the embodiments above, double stranded, single stranded (ssRNA) and hairpin (shRNA) interfering RNAs suitable for silencing the expression of the desired gene.

Examples of making and using such hairpin RNAs for silencing in mammalian cells are described in McCaffrey at al. Nature 2002 (see below for detail).

Interfering RNAs (double or single strand or hsRNA) may be synthesized chemically or expressed endogenously from viral or plasmid vectors or expression cassettes. Examples of commercially available plasmid-based expression vector include members of pSilencer series (Ambion, Austin Tex.) and pCpG-siRNA (InvivoGen, San Diego). Viral vector for interfering RNA may be drived from varieties of viruses including retrovirus, adenovirus, lentivirus, baculovirus and herpes virus. Examples of commercially available viral vectors for interfering RNA include pSilencer adeno (Ambion, Austin Tex.) and pLenti6/BLOCK-iT™-DEST (Invitrogen). Selections of plasmid or viral vector, methods for expressing interfering RNA from the vector are within the ordinary skills of one in the art.

Interfering RNAs may be different form the naturally-occurring RNA by the addition, deletion, substitution of one or more nucleotides. Non-nucleotides material may be bound to siRNA in order to increase nuclease resistance, to improve cellular uptake, to enhance cellular targeting, to further improve stability.

In particular, mechanisms to delivery siRNA to the target molecules and cells include viral or plasmid vectors, liposomes, nanoparticles but also chemical modifications.

Liposomes and nanoparticles represent efficient delivery systems in vivo and in vitro.

Unmodified siRNA has a half-life of less than 1 hour in human plasma and siRNA is rapidly excreted by the kidneys. Liposomes and nanoparticles can act as envelopes to protect the siRNA from metabolism and excretion, but can also carry specific molecules designed to target the siRNA to specific tissue types. Liposomes made of cationic lipids such as DOTAP (1,2-bis(oleoyloxy)-3,3-(trimethylammonium) propane), neutral lipids such as DOPE (dioleoylphosphatidylethanolamine) may be used to carry siRNA into cells.

Nanoparticles such as the cationic polymer, polyethyleneimine (PEI) may be used to successfully deliver siRNA to target cells.

Instead, examples of chemical modifications include a 3' terminal biotin molecule, a peptide to known to have cell penetrating properties, or 3' cholesterol conjugation. Furthermore, it is possible to modify either the phosphate-sugar backbone or the nucleotide so, by way of example, the phosphodiester linkages of natural RNA may be modified to include at least one heteroatom (phosphotothioate, phosphoramidate etc).

In order to allow the entry of siRNAs into the target cells, trasfection reagents such as Lipofectamine, Lipofectin may be used.

However, any routine suitable method or chemical modification, comprising in the art and known to the skilled person, for delivering and/or enhancing the ability of siRNA (dsRNAs, ssRNAs, hsRNA, expression RNAi vector) to pass the cell membrane, and thus elicit its biological activity, is part of the present description.

Various strategies for delivering siRNA to specific tissue and organ systems in vivo and in vitro may be used, including the direct local injection of siRNA into a pre neoplastic or neoplastic lesion. Alternatively, the siRNA, for example, formulated with liposomes can be associated with one or more ligands effective to bind to a specific surface cell protein on the target cell, thereby enhancing, in some case, uptake of the siRNA by the cells. Merely to illustrate, folate, VEGF, EGF are examples of ligands suitable for targeting epithelial carcinoma.

According to the present description, siRNAs (dsRNA, ssRNA, shRNA and expressing siRNA vector) are used in a treatment for inhibiting the invasiveness of a pre neoplastic or neoplastic lesion or cells thereof.

In another embodiment of the invention, the polyclonal or monoclonal antibody binding hMenaΔv6 isoform protein may be used in a treatment for inhibiting of the invasiveness of a pre neoplastic or neoplastic lesion or cells thereof.

In particular, said polyclonal or monoclonal antibody or fragments thereof specifically binding a protein having SEQ ID NO: 2 or a fragment thereof specific for hMenaΔv6 isoform or a peptide having SEQ ID NO: 3.

Polyclonal or monoclonal antibodies according to the present invention are described in detail above.

The invention still further provides a method for the inhibition of the invasive behaviour of a pre neoplastic or neoplastic lesion or cells thereof comprising the step of inhibiting the expression or the functionality or the oligomerisation of hMena Δv6.

The method may involve intervention at DNA, RNA or protein level by using suitable inhibitors. hMena Δv6 isoform interacts with the other hMena isoforms and with other members of Ena/VASP family to form functional tetramers which regulate actin cytoskeleton dynamics Inhibition of hMenaΔv6 inclusion into the tetramers or exogeneous inclusion of hMena11a may change the function of the tetramer in terms of actin network and ultimately in the ability of the cell to invade.

Thus, the inhibition of hMena Δv6 may be achieved by using for example, siRNAs, antibodies or aptamers, as described above. These inhibitors may be added directly or indirectly on either a biological sample or lesion to be treated both in vitro and in vivo.

An embodiment of the present invention is also a pharmaceutical composition comprising at least one inhibitor of hMena Δv6 expression or functionality or oligomerisation and at least a pharmaceutically acceptable carrier and/or excipient.

Pharmaceutical composition according to the present invention may comprise inhibitors such as siRNAs and/or antibodies and/or aptamers specific for the hMena Δv6 isoform.

The composition will be formulated for delivering a therapeutically effective amount of said inhibitors to a target site.

In particular, composition comprising siRNAs within said siRNAs or salt thereof may be formulated, for example, in cationic or neutral lipids vehicles, liposomes, polymers, nanoparticles. The administration may be carried out by any means suitable for delivering the siRNA to the target site known in the art. For example, siRNA may be administrated by electroporation, or by other suitable parental or enteral administration routes. Suitable administration routes, for example, include intravascular administration; intra-tissue administration (e.g. intra-tumour or intra-lesion injection); direct application to the area or near the area of the target site; inhalation. One skilled in the art can also readily define the appropriate administration routes according to the target site to be reached. The present pharmaceutical composition comprises the siRNAs of the invention (e.g. 0.1 to 90% in weight) or a physiological acceptable salt thereof, mixed with a physiologically acceptable carrier such as water, buffer, saline solution, glycine, hyaluronic acid, mannitol, lactose, glucose and the like. Said compositions also comprise pharmaceutical excipients and/or additives such as stabilizers, antioxidants, osmolality adjusting agents, pH adjusting agents. Pharmaceutical composition comprising siRNAs can be also lyophilized.

Alternatively, the pharmaceutical composition comprises an antibody capable of specifically binding (and inhibiting the functionality or the mere capability to oligomerise) the Δv6 isoform of the hMena protein. In one embodiment of the invention said antibody binds the amino acid sequence of SEQ ID NO: 2 coding for the Δv6 isoform of hMena or fragments thereof comprising the amino acids from 267 to 270.

Pharmaceutical compositions comprising said antibody are prepared by mixing the antibody having the desire degree of purity with one or more pharmaceutical acceptable carrier and/or excipient and/or stabilizer.

Acceptable carriers or excipients or stabilizers include buffer such as phosphate, citrate, and other organic acid, antioxidants such as ascorbic acid and methionine; preservatives; proteins such as serum albumin, gelatine; monosaccharides, disaccharides, glucose, mannose, dextrin, sorbitol. Methods for preparing pharmaceutical composition comprising antibody and acceptable carriers and/or excipients and/or stabilizers are well known to the skilled person that, without inventive skill, is capable to prepare a pharmaceutical composition according to the present invention.

The antibody may be entrapped in drug delivery system, for example, liposomes, nanoparticles, albumine microspheres in order to induce the internalization by target cells resulting in therapeutic effective of the pharmaceutical composition.

The pharmaceutical composition comprising said antibody according to the present invention may be administered in any suitable administration way including parental, enteral, namely intramuscular, subcutaneous, intravenous, intraarterial, topic, nasal, buccal, etc administration. Said composition will be formulated, dosed and administrated by the skilled person taking into account, for example, the target site to be reached, the clinical conditions of the patient to be treated.

The invention also provides a method for the screening of a candidate compound that inhibits the invasive behaviour of a pre neoplastic or neoplastic lesion or cells thereof comprising the step of contacting the compound with a cell line or tissue culture expressing the hMena Δv6 isoform of hMena, wherein the reduction in the expression of said isoform or its displacement from Ena/VASP tetramers is indicative that the compound is a candidate compound for inhibiting the invasive behaviour of a pre neoplastic or neoplastic lesion or cells thereof.

In other words, lack of reduction (or conversely the increase) in expression of hMena Δv6 isoform or its displacement in said lesion or cells, following contact with a compound, indicates that the compound is not a suitable candidate molecule for inhibiting the invasive behaviour of a pre neoplastic or neoplastic lesion or cells thereof.

Since, hMena has been isolated as a tumor antigen able to induce an antibody response in neoplastic patients and not in healthy donors, the present invention also provides a method for the detection of antibodies specific for each hMena isoform from the sera of preneoplastic or neoplastic cancer patients. Presence of specific antibodies in the sera of patients may represent not only an early marker of cancerogenesis but also may help in the understanding the proliferative or invasive behaviour of the tumor, helping the clinicians in the correct choice of efficacious therapeutic treatment.

The present invention is illustrated in the following experiments, which are set forth to aid in the understanding of the invention, and should not to be intended to limit in any way the scope of the invention herein described.

EXAMPLES

Example 1: Molecular Cloning and Characterization of hMenaΔv6 Coding Sequence

Figure 1:
FIG. 1. hMenaΔv6 isoform variant.
Figure 1:
Figure 1:
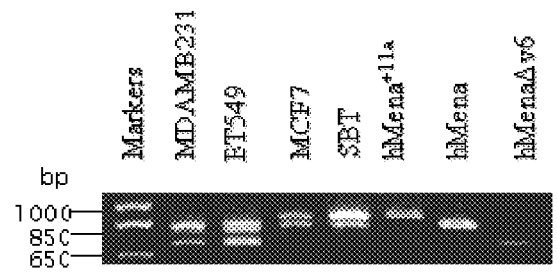

RT-PCR experiments on the breast cancer cell line MDA-MB-231 with two primers designed on the human Mena coding sequence and possessing the ATG and the stop codon respectively were performed. PCR products sequencing revealed that these cells express hMena (1713nt) and in addition, a not yet described transcript of 1602 nucleotides from the ATG to the stop codon. This sequence is identical to hMena, but lacks the internal exon 6 of 111 nucleotides, thus we named this splice variant hMena Δv6 (GenBank, Accession: 1030575), SEQ ID NO: 1.

hMena Δv6 cDNA encodes a protein of 533aa (SEQ ID NO: 2) without an internal peptide of 37aa located between the LERER and the Proline-rich region of hMena (FIG. 1). The absence of this peptide physically approaches, in the protein, the LERER domain with the pro-rich domain. Upon protein alignment, hMena Δv6 displays an identity of 88% with the 526aa Rattus norvegicus ENAH (NCBI Accession: AAH83927), being the majority of the divergences located in the LERER domain; 87% with the 513aa avenaII from Gallus gallus (NCBI Accession: BAB18909) and 77% with the 535aa enabled protein from Xenopus laevis (NCBI Accession: AAW31125). NCBI database does not include mouse or human complete sequences showing the lack of exon 6, but EST database revealed two mouse sequences, from embryonic stem cells (Accession: AV470522) and from mammary infiltrating ductal carcinoma (Accession: BI664046) and one human sequence from duodenal adenocarcinoma cell line (Accession: BF982593).

At protein level the Western analysis of hMena and hMena Δv6 in vitro translated proteins by the use of an anti-hMena antibody recognizing all the isoforms (pan-hMena) revealed that, as shown in FIG. 1 panel B the proteins migrate with an apparent molecular weight of 88 kDa (hMena) and 80 kDa (hMena Δv6), whereas the predicted molecular weight is 66 kDa and 60 kDa, respectively. This slower mobility may be attributed to the proline-rich motif present in the sequence. As shown in FIG. 1 panel B the two in vitro translated hMena and hMena Δv6 isoforms correspond to the bands revealed by Western blot analysis in MDA-MB-231 tumour cell protein extracts.

Example 2: hMena11a and hMena Δv6 are Alternatively Expressed and Correlate with an Epithelial and Mesenchymal Phenotype Respectively We then analyzed by RT-PCR experiments the expression of hMena, hMena11a and hMenaΔv6 by two primers located in the exons 5 and 12 respectively (MTC1f; MTC4r) on a panel of breast cancer cell lines. Whereas hMena is always present, the two splice variants hMena11a and hMena Δv6 are mutually exclusive expressed (FIG. 1 panels B, C). As shown in the FIG. 1, two luminal breast cancer cell lines MCF7 and SBT express hMena11a and not hMena Δv6, which is conversely present in basal breast cancer cells MDA-MB-231 and BT549, lacking the epithelial hMena11a isoform, suggesting that the hMena Δv6 expression is peculiar of mesenchymal phenotype.

At protein level the characterization of hMena isoform expression lines with specific antibodies we produced demonstrate, in a large panel of cell, that hMena11a and hMena Δv6 correlate with an epithelial or mesenchymanl phenotype respectively (FIG. 2 panel A). Normal human keratinocytes expressed hMena11a and E-Cadherin whereas fibroblast expressing N-cadherin are negative for hMena11a and expressed hMena Δv66. Normal cells showed a very low level of hMena expression and platelets were negative as described (Gertler F B, Niebuhr K, Reinhard M, Wehland J, Soriano P. Mena, a relative of VASP and Drosophila Enabled, is implicated in the control of microfilament dynamics Cell. 1996 Oct. 18; 87(2):227-39.). All the breast and lung cancer cell lines expressing hMena11a show a concomitant expression of E-Cadherin. Only DAL cells expressing E-Cadherin expresses a very low level of hMena11a. Conversely, the lack of hMena11a expression is always correlated with the absence of E-Cadherin with the exception of SKBr3 cells in which the absence of E-Cadherin is due to a gene mutation. In these cells no expression of hMena Δv6 was revealed, whereas all the breast and lung cancer cell lines with a lack of E-Cadherin and positive for mesenchymal markers as N-Cadherin were hMena11a negative and expressed hMena Δv6.

Glyoma and melanoma are highly invasive forms of neoplasia, and we tested the hMena isoforms expression in 6 melanoma and 3 glioma cell lines (T98G, U87MG, U373). Five out of six melanoma cell lines show hMena Δv6 expression in concomitance with N-Cadherin (ME10538 shows a very faint hMena Δv6 signal). The only melanoma cell line (1007) expressing E-Cadherin doesn't express hMena Δv6. All the glioma cell lines tested are positive for hMena Δv6 and negative for hMena11a as revealed by the use of anti-hMena11a antibody (FIG. 2 panel A). The hMena isoform (88 kDa) is always expressed with the exception of platelets, as detected by the pan-hMena Ab.

Collectively, these results indicate that hMena11a expression identifies an epithelial cell phenotype. In line with these results, it has been recently reported that the epithelial specific regulators proteins (ESRPs) are able to induce the inclusion of 11a exon in hMena RNA transcripts of the hMena11a negative MDA-MB-231 cells (Warzecha C C, Sato T K, Nabet B, Hogenesch J B, Carstens R P. ESRP1 and ESRP2 are epithelial cell-type-specific regulators of FGFR2 splicing. Mol Cell. 2009; 33:591-601).

Example 3: hMena11a Transfection Inhibits Matrigel Invasion of hMena11a Negative Breast Cancer Cells In order to understand whether the lack of hMena11a contributes to the invasive and migratory behaviour of hMena Δv6 expressing cells, we have transfected MDA-MB-231 cells with hMena11a. Matrigel invasion assays, demonstrate a very significant inhibition of invasion in MDA-MB-231-hMena11a transfected cells respect to the control (FIG. 6 panel A). In addition, results of wound healing migration assay clearly show that, in contrast to the behaviour of control cells (pcDNA3), MDA-MB-231-hMena11a transfected cells do not scatter and do not migrate into the wound either after 24 h or, more evident after 48 h. A significant reduction of the invasive properties determined by hMena11a transfection was also observed in the highly invasive BT549 cells, as shown in FIG. 6 panel B.

Immunofluorescence analysis (FIG. 6 panel D) show cytoskeletal changes following the exogeneous expression of hMena11a. In BT549 is evident a different pattern of actin organization in the transfected cells respect to the control. The actin fibres network decorated with phalloidin assumes a cortical localization in the transfected cells. This pattern is similar to the one observed in hMena11a expressing luminal MCF7 cells, thus suggesting that hMena11a may be pivotal for the remodelling of peripheral actin filaments.

Example 4: hMena/hMenaΔv6 Knock Down Reduces and hMenaΔv6 Transfection Increases the Cell Migration and Invasion of Breast Cancer Cell Lines hMena11a Negative At functional level we have previously shown that hMena11a overexpression and phosphorylation leads to increased p42/44 mitogen-activated protein kinase (MAPK) activation and cell proliferation as evidenced in hMena11a transfected breast cancer cell lines.

The two basal breast cancer cell lines (MDA-MB-231, BT549) expressing hMenaΔv6 and lacking hMena11a, show a stellate morphology and an invasive and migratory behaviour. To evaluate whether hMenaΔv6 affect the migratory and invasive behaviour of the cells, we have knock-down hMena/hMenaΔv6 expression by siRNA (SMART pool si-ENAH, Dharmacon) in MDA-MB-231 and BT549 cells for 72 h. Wound healing migration assay was performed on MDA-MB-231 cells during the last 24 hours of transfection and the results indicate that the knock-down of hMena/hMenaΔv6 reduced the migration of MDA-MB-231 cells.

The ability of invasion has been measured in the highly invasive BT549 transfected with hMena/hMenaΔv6 siRNA. We have evaluated the ability of invasion during the last 24 h of transfection by the use of Matrigel coated transwell filters (BD Biosciences) toward a gradient of EGF or FBS. As shown in FIG. 5, hMena/hMenaΔv6 knock-down strongly reduced the invasive ability of BT549 cells, either using FBS or EGF as chemoattractant.

Since hMena/hMenaΔv6 knock down inhibits cell migration and invasion of hMenaΔv6 expressing cells we have transfected this isoform in the MDA-MB-231 cells as well as in the hMenaΔv6 negative DAL and MCF7 cells. Results reported in FIG. 6 indicate a significant higher number of invading cells in the population of MDA-MB-231-hMenaΔv6 stably transfected cells respect to the control (p=0.0023). Similarly, in the hMena11a/hMenaΔv6 negative DAL cells a strong induction in the invasive behaviour of the cells is observed following hMenaΔv6 transfection. On the contrary, the exogeneous expression of hMenaΔv6 does not induce a migratory or invasive behaviour in the MCF7 cells expressing hMena11a as evaluated by wound healing (not shown) and invasion assays, thus suggesting that the presence of hMena11a plays a dominant anti-invasive role respect to the other hMena isoforms.

This result, i.e. the alternative expression of said two splice variants, is confirmed by experiments wherein the transfection of hMenaΔv6 in cancer cell lines negative for hMena11a induces an increase in the migratory and invasive behaviour of the cells. On the contrary, hMena11a exogenous expression induces an increase in the cell proliferative ability. Interestingly, over expression of hMena11a in cancer cells expressing hMenaΔv6, induces a inhibition or a significant reduction of hMenaΔv6 isoform expression as shown in FIG. 2B.

Experimental Section

Cell Lines

The following cell lines were purchased from the American Type Culture Collection (ATCC, Rockville, Md.): MDAMB468, MDAMB361, T47D, SKBr3, MCF7, BT474, MDA-MB-231 and BT549 (breast cancer), A549, AE2, H1299, Calu3 (lung cancer), T98G, U87MG and U373 (glioma). Other cell lines employed were: melanomas, 4405 and 1007 were developed in our laboratory from a primary melanoma lesion. DAL developed in our laboratory from the ascitic fluid of two breast cancer patients; normal human keratinocytes (NHK) and normal human fibroblasts (NHF) were kindly provided by Dr. A. Venuti (Regina Elena Cancer Institute, Rome, Italy) respectively; melanoma ME10538, VAS, 3046, 4405 and 1007 were kindly provided by Dr. A. Anichini (Istituto Tumori Milano, Italy).

Cloning and Sequencing of hMena and hMena Δv6

Two micrograms of total RNA extracted from the MDA-MB-231 cell line using Trizol reagent (Life Technologies Inc, Rockville, Md., USA) was used to obtain the relative cDNA by first strand cDNA synthesis kit (Amersham Pharmacia Biotech, Little Chalfont, UK). cDNA was amplified using Platinum Pfx DNA polymerase (Invitrogen) in PCR reactions consisting of 30 cycles at a denaturation temperature of 94° C. (30 sec/cycle), an annealing temperature of 55° C. (1 min/cycle) and an extension temperature of 68° C. (3 min/cycle). The primers utilized (Invitrogen) contained the ATG and stop-codon of hMena, P1-ATG (5'-CACCATGAGTGAACAGAGTATC-3') SEQ ID NO: 11 and P8-stop (5'-CTGTTCCTCTATGCAGTATTTGAC-3') SEQ ID NO: 12. PCR products were analyzed on a 1% agarose gel, excised from the gel and purified using a gel extraction kit (Qiagen, Crawley, UK). Samples were incubated with 1 unit of AmpliTaq polymerase and 1 μl of 10 mM dATP (both, Applied Biosystems, Branchburg, N.J., USA) to add 3' adenines and then cloned by pcDNA3.1/V5-HIS TOPO TA Expression kit (Invitrogen). Plasmid DNA was isolated by Wizard Plus minipreps DNA purification system (Promega Corporation, Madison, Wis., USA) and sequenced initially by T7 and T3 primers. Once the initial sequences were obtained, additional primers were synthesized to sequence into the insert (P4-for 5'-GAGCGACTG-GAACAAGAACAGCTG-3' SEQ ID NO: 13; P5-for 5'-GAGAG-CGCAGAATATCAAGTGCTG-3' SEQ ID NO: 14; P6-rev 5'-GGCGATTGTCTT-CTGACATGG-3' SEQ ID NO: 15; P7-for 5'-GAATTGCTGAAAAGGGATC-3' SEQ ID NO: 19; P7-rev 5'-GATCCCTTTTCAGCAATTC-3' SEQ ID NO: 16). DNA sequencing was performed by the Nucleic Acid Facility Service (Istituto Dermopatico dell'Immacolata, Rome, Italy) with the use of an ABI PRISM 377-96 automated sequencer (Applied Biosystem).

RT-PCR hMena splice variants were detected by RT-PCR using MTC1f (5'-GCTGGAATGGGAGAGAGAGCGCA-GAATATC-3' SEQ ID NO: 20) and MTC4r (GTCAAGTC-CTTCCGTCTGGACTCCATTGGC-3' SEQ ID NO: 21) primers. PCR reactions consisted of 30 cycles at a denaturation temperature of 94° C. (30 sec/cycle), an annealing and an extension temperature of 68° C. (2 min/cycle). PCR products were analyzed on a 1% agarose gel electrophoresis and ethidium bromide staining.

In Vitro Transcription-Coupled Translation

The in vitro translation of the hMena and hMena Δv6 cDNA (inserted into the pcDNA3.1 vector) was examined in an in vitro transcription-coupled translation system following the manufacture's instruction (TNT, rabbit reticulocyte lysate system, Promega Corporation).

Antibodies

The rabbit polyclonal antibody specific for the hMena11a isoform was developed against an 18-aa peptide (RD-SPRKNQIVFDNRSYDS, SEQ ID NO: 10) of the 11a sequence peculiar of this isoform by the use of Primm Service (Primm srl, Milan, Italy). To obtain antibodies specific for the hMenaDv6 isoform rabbits were immunized with a peptide coded by a region covering the 5 and 7 exon junction (SEQ ID NO: 3). The rabbit antiserum was then purified by two steps of affinity chromatography using peptides coded by the 5 and 6 exon junction or by the 6 and 7 exon junction (SEQ ID NOS: 4 and 5) in order to deplete the serum from the antibodies recognizing regions common to all the hMena isoforms. The specific IgGs were then purified using the immunogenic peptide (SEQ ID NO: 3) by affinity chromatography. The specificity of the antibodies obtained was evaluated by Western blot on MCF7 (hMena11a positive hMena Δv6 negative) and MDA-MB-231 (hMena11a negative, hMena Δv6 positive) cells (FIG. 2) as well as on DAL cells transfected with hMena11a, hMena Δv6 or with the empty vector (not shown), and by immunohistochemistry abolishing the antibodies' reactivity against breast cancer tissues by the pretreatment with the immunogenic peptide (FIG. 7).

Western Blot Analysis

Cells were lysed as reported. Lysates (30 μg or 50 μg) were resolved on 10% polyacrylamide gel and transferred to nitrocellulose membrane (Amersham Bioscience) as described. Blots were probed with the following antibodies: 10 μg/ml of anti-hMena rabbit CKLK1 antibody; anti-hMena11a (0.5 μg/ml) and anti-hMena Δv6 (0.6 μg/ml); mouse anti-E-Cadherin from BD Biosciences; mouse anti-N-Cadherin from DakoCytomation (Glostrup, Denmark) in 3% skimmed milk/TBST overnight at 4° C. For actin signal, blots were reprobed with 1 μg/ml monoclonal anti-actin, mouse-ascites Fluid clone AC-40 (Sigma Aldrich, Poole, UK).

Western blot analysis was also performed on 5 μl of in vitro translated hMena and hMena Δv6.

Immunofluorescence Analysis

Cells grown on glass coverslips to semiconfluence coated with 100 μg/ml Rat Tail Collagen Type 1 (BD Biosciences San Jose, Calif., USA) were fixed in 4% paraformaldehyde (EMS, Fort Washington, Pa., USA) for 15 minutes, permeabilized with 0.2% Triton X-100 in PBS. Following incubation with 1% (w/v) bovine serum albumin (Sigma, St. Louis, Mo., USA) cells were incubated for 1 hour Phalloidin labelled with AlexaFluor 532 (Life Technologies/Invitrogen), washed with PBS and mounted with H-1200 Vectashield mounting medium containing 4',6-diamidino-2-phenylindole (DAPI) (Vector Laboratories Inc., Burlingame, Calif., USA). The images are representative of two independent experiments done in duplicate.

Transfections and Small-Interfering RNA Treatment

Cells in exponential growth phase were plated in 6-well plates at a density of 3×105 cells/well. After 24 h cells were transfected with 1.5 µg/ml hMena+11a, hMena Δv6 cDNA or with vector alone (pcDNA3) or with 100 nmol/L hMena-specific pooled siRNA duplexes (siENA SMART pool) or control non-specific siRNA (Dharmacon, Lafayette, Colo.) using LipofectAMINE 2000 reagent (Invitrogen) according to the protocol of the manufacturer. Stable transfectants were obtained by selecting transfected cells with 500 µg/ml of G418 (Invitrogen, Pisley, UK) in complete culture medium.

Wound-Healing Assay

Cells were seeded on 6-well plates and transfected with the indicated siRNA. Forty-eight hours after transfection the confluent cells were scratched with a pipette tip. In other cases cells were grown to confluence in 6-well plates and then scratched. Depending on the cell type, the cells were photographed after 24 h and 48 h using an inverted microscope. Each experiment was performed in triplicate and repeated at least three times. Cells were then lysate and analyzed in Western blot to ascertain the efficiency of the siRNA transfection.

Cell Invasion Assay

Forty-eight hours after siRNA transfection cells were counted and equal numbers were seeded to Matrigel invasion chamber (24 wells; BD Biocoat Matrigel invasion chamber, BD, Biosciences) in duplicate following the manufacturer's instruction. Cells were allowed to invade for 24 h and in some cases for 72 h, then were stained, photographed and counted. Each experiment was performed thrice.

Statistical Analysis

All experiments were repeated a minimum of three times. Data collected from invasion assays incorporation assay were expressed as means±SD. The data presented in some figures are from a representative experiment, which was qualitatively similar in the replicate experiments. Statistical significance was determined by Student's t test (two tailed) comparison between two groups of data sets. Asterisks indicate significant differences of experimental groups compared with the corresponding control condition (P<0.05, see figure legends). Statistical analysis was performed using GraphPad Prism 4, V4.03 software (GraphPad Inc., San Diego, Calif.).

```
SEQUENCE LISTING
Splice variant Δv6 of hMena
                                                                    (SEQ ID NO: 1)
atg agt gaa cag agt atc tgt cag gca aga gct gct gtg atg gtt tat gat gat gcc aat aag aag tgg gtg cca gct ggt ggc tca act gga ttc agc aga gtt cat atc tat cac cat aca ggc aac aac aca ttc aga gtg gtg ggc agg aag att cag gac cat cag gtc gtg ata aac tgt gcc att cct aaa ggg ttg aag tac aat caa gct aca cag acc ttc cac cag tgg cga gat gct aga cag gtg tat ggt ctc aac ttt ggc agc aaa gag gat gcc aat gtc ttc gca agt gcc atg atg cat gcc tta gaa gtg tta aat tca cag gaa aca ggg cca aca ttg cct aga caa aac tca caa cta cct gct caa gtt caa aat ggc cca tcc caa gaa gaa ttg gaa att caa aga aga caa cta caa gag cag caa cgg caa aag gag ctg gag cgg gaa agg ctg gag cga gaa aga atg gaa aga gaa agg ttg gag aga gag agg tta gaa agg gaa agg ctg gag agg gag cga ctg gaa caa gaa cag ctg gag aga gag aga caa gaa cgg gaa cgg cag gaa cgc ctg gag cgg cag gaa cgc ctg gag cgg cag gaa cgc ctg gag cgg cag gaa cgc ctg gat cgg gag agg caa gaa aga caa gaa cga gag agg ctg gag aga ctg gaa cgg gag agg caa gaa agg gag cga caa gag cag tta gaa agg gaa cag ctg gaa tgg gag aga gag cgc aga ata tca agt gct ggc att gtc ttg gga cca ctt gca cct cca cct cct cca cca ctc cca cca ggg cct gca cag gct tca gta gcc ctc cct cct ccc cca ggg ccc cct cca cct cct cca ctc cca tcc acc ggg cct cca ccg ccc cct cct ccc cct cct ctc cct aat caa gta ccc cct cct cct cca cca cct cct gcc cca ccc ctc cct gca tct gga ttc ttt ttg gca tcc atg tca gaa gac aat cgc cct tta act gga ctt gca gct gca att gcc gga gca aaa ctt agg aaa gtg tca cgg atg gag gat acc tct ttc cca agt gga ggg aat gct att ggt gtg aac tcc gcc tca tct aaa aca gat aca ggc cgt gga aat gga ccc ctt cct tta ggg ggt agt ggt tta atg gaa gaa atg agt gcc ctg ctg gcc agg agg aga aga att gct gaa aag gga tca aca ata gaa aca gaa caa aaa gag gac aaa ggt gaa gat tca gag cct gta act tct aag gcc tct tca aca agt aca cct gaa cca aca aga aaa cct tgg gaa aga aca aat aca atg aat ggc agc aag tca cct gtt atc tcc aga cca aaa tcc aca ccc tta tca cag ccc agt gcc aat gga gtc cag acg gaa gga
```

-continued

```
ctt gac tat gac agg ctg aag cag gac att tta gat gaa atg aga aaa gaa tta aca aag cta aaa gaa
gag ctc att gat gca atc agg cag gaa ctg agc aag tca aat act gca tag
```

Amino acid sequence of Δv6 hMena isoform (SEQ ID NO: 2)

```
Met Ser Glu Gln Ser Ile Cys Gln Ala Arg Ala Ala Val Met Val Tyr Asp Asp Ala Asn
Lys Lys Trp Val Pro Ala Gly Gly Ser Thr Gly Phe Ser Arg Val His Ile Tyr His His
Thr Gly Asn Asn Thr Phe Arg Val Val Gly Arg Lys Ile Gln Asp His Gln Val Val Ile
Asn Cys Ala Ile Pro Lys Gly Leu Lys Tyr Asn Gln Ala Thr Gln Thr Phe His Gln Trp
Arg Asp Ala Arg Gln Val Tyr Gly Leu Asn Phe Gly Ser Lys Glu Asp Ala Asn Val
Phe Ala Ser Ala Met Met His Ala Leu Glu Val Leu Asn Ser Gln Glu Thr Gly Pro Thr
Leu Pro Arg Gln Asn Ser Gln Leu Pro Ala Gln Val Gln Asn Gly Pro Ser Gln Glu Glu
Leu Glu Ile Gln Arg Arg Gln Leu Gln Glu Gln Gln Arg Gln Lys Glu Leu Glu Arg Glu
Arg Leu Glu Arg Glu Arg Met Glu Arg Glu Arg Leu Glu Arg Glu Arg Leu Glu Arg
Glu Arg Leu Glu Arg Glu Arg Leu Glu Gln Glu Gln Leu Glu Arg Glu Arg Gln Glu
Arg Glu Arg Gln Glu Arg Leu Glu Arg Gln Glu Arg Leu Glu Arg Gln Glu Arg Leu
Glu Arg Gln Glu Arg Leu Asp Arg Glu Arg Gln Glu Arg Gln Glu Arg Glu Arg Leu
Glu Arg Leu Glu Arg Glu Arg Gln Glu Arg Glu Arg Gln Glu Gln Leu Glu Arg Glu
Gln Leu Glu Trp Glu Arg Glu Arg Arg Ile Ser Ser Ala Gly Ile Val Leu Gly Pro Leu
Ala Pro Pro Pro Pro Pro Leu Pro Gly Pro Ala Gln Ala Ser Val Ala Leu Pro
Pro Pro Pro Gly Pro Pro Pro Pro Pro Leu Pro Ser Thr Gly Pro Pro Pro Pro Pro
Pro Pro Pro Leu Pro Asn Gln Val Pro Pro Pro Pro Pro Pro Ala Pro Pro Leu
Pro Ala Ser Gly Phe Phe Leu Ala Ser Met Ser Glu Asp Asn Arg Pro Leu Thr Gly Leu
Ala Ala Ala Ile Ala Gly Ala Lys Leu Arg Lys Val Ser Arg Met Glu Asp Thr Ser Phe
Pro Ser Gly Gly Asn Ala Ile Gly Val Asn Ser Ala Ser Ser Lys Thr Asp Thr Gly Arg
Gly Asn Gly Pro Leu Pro Leu Gly Gly Ser Gly Leu Met Glu Glu Met Ser Ala Leu Leu
Ala Arg Arg Arg Arg Ile Ala Glu Lys Gly Ser Thr Ile Glu Thr Glu Gln Lys Glu Asp
Lys Gly Glu Asp Ser Glu Pro Val Thr Ser Lys Ala Ser Ser Thr Ser Thr Pro Glu Pro
Thr Arg Lys Pro Trp Glu Arg Thr Asn Thr Met Asn Gly Ser Lys Ser Pro Val Ile Ser
Arg Pro Lys Ser Thr Pro Leu Ser Gln Pro Ser Ala Asn Gly Val Gln Thr Glu Gly Leu
Asp Tyr Asp Arg Leu Lys Gln Asp Ile Leu Asp Glu Met Arg Lys Glu Leu Thr Lys
Leu Lys Glu Glu Leu Ile Asp Ala Ile Arg Gln Glu Leu Ser Lys Ser Asn Thr Ala
```

Immungenic peptide used to obtain anti-deltav6 antibody (SEQ ID NO: 3)

Glu Arg Arg Ile Ser Ser Ala Gly Ile Val Leu Gly

Peptide used in affinity chromatography for separating the Δv6 specific antibody coded by the 5 and 6 junction (SEQ ID NO: 4)

Glu Trp Glu Arg Glu Arg Arg Ile Ser Ser Ala Ala Ala

Peptide used in affinity chromatography for separating the Δv6 specific antibody coded by the 6 and 7 junction (SEQ ID NO: 5)

Ser Gln Gln Gly Ile Val Leu Gly Pro Leu Ala Pro Pro

Nucleotide sequence of splice variant 11a of hMena (SEQ ID NO: 6)

atg agt gaa cag agt atc tgt cag gca aga gct gct gtg atg gtt tat gat gat gcc aat aag aag tgg gtg cca gct ggt ggc tca act gga ttc agc aga gtt cat atc tat cac cat aca ggc aac aac aca ttc -continued aga gtg gtg ggc agg aag att cag gac cat cag gtc gtg ata aac tgt gcc att cct aaa ggg ttg aag tac aat caa gct aca cag acc ttc cac cag tgg cga gat gct aga cag gtg tat ggt ctc aac ttt ggc agc aaa gag gat gcc aat gtc ttc gca agt gcc atg atg cat gcc tta gaa gtg tta aat tca cag gaa aca ggg cca aca ttg cct aga caa aac tca caa cta cct gct caa gtt caa aat ggc cca tcc caa gaa gaa ttg gaa att caa aga aga caa cta caa gaa cag caa cgg caa aag gag ctg gag cgg gaa agg ctg gag cga gaa aga atg gaa aga gaa agg ttg gag aga gag agg tta gaa agg gaa agg ctg gag agg gag cga ctg gaa caa gaa cag ctg gag aga gag aga caa gaa cgg gaa cgg cag gaa cgc ctg gag cgg cag gaa cgc ctg gag cgg cag gaa cgc ctg gag cgg cag gaa cgc ctg gat cgg gag agg caa gaa aga caa gaa cga gag agg ctg gag aga ctg gaa cgg gag agg caa gaa agg gag cga caa gag cag tta gaa agg gaa cag ctg gaa tgg gag aga gag cgc aga ata tca agt gct gct gcc cct gcc tct gtt gag act cct cta aac tct gtg ctg gga gac tct tct gct tct gag cca ggc ttg cag gca gcc tct cag ccg gcc gag act cca tcc caa cag ggc att gtc ttg gga cca ctt gca cct cca cct cct cca cca ctc cca cca ggg cct gca cag gct tca gta gcc ctc cct cct ccc cca ggg ccc cct cca cct cct cca ctc cca tcc acc ggg cct cca ccg ccc cct cct ccc cct cct ctc cct aat caa gta ccc cct cct cct cca cca cct cct gcc cca ccc ctc cct gca tct gga ttc ttt ttg gca tcc atg tca gaa gac aat cgc cct tta act gga ctt gca gct gca att gcc gga gca aaa ctt agg aaa gtg tca cgg atg gag gat acc tct ttc cca agt gga ggg aat gct att ggt gtg aac tcc gcc tca tct aaa aca gat aca ggc cgt gga aat gga ccc ctt cct tta ggg ggt agt ggt tta atg gaa gaa atg agt gcc ctg ctg gcc agg agg aga aga att gct gaa aag gga tca aca ata gaa aca gaa caa aaa gag gac aaa ggt gaa gat tca gag cct gta act tct aag gcc tct tca aca agt aca cct gaa cca aca aga aaa cct tgg gaa aga aca aat aca atg aat ggc agc aag tca cct gtt atc tcc aga cgg gat tct cca agg aaa aat cag att gtt ttt gac aac agg tcc tat gat tca tta cac aga cca aaa tcc aca ccc tta tca cag ccc agt gcc aat gga gtc cag acg aag gac tta gac tat gac agg ctg aag cag gac att tta gat gaa atg aga aaa gaa tta aca aag cta aaa gaa gag ctc att gat gca atc agg cag gaa ctg agc aag tca aat act gca tag Amino acid sequence of isoform 11a of hMena
(SEQ ID NO: 7)

Met Ser Glu Gln Ser Ile Cys Gln Ala Arg Ala Ala Val Met Val Tyr Asp Asp Ala Asn

Lys Lys Trp Val Pro Ala Gly Gly Ser Thr Gly Phe Ser Arg Val His Ile Tyr His His

Thr Gly Asn Asn Thr Phe Arg Val Val Gly Arg Lys Ile Gln Asp His Gln Val Val Ile

Asn Cys Ala Ile Pro Lys Gly Leu Lys Tyr Asn Gln Ala Thr Gln Thr Phe His Gln Trp

Arg Asp Ala Arg Gln Val Tyr Gly Leu Asn Phe Gly Ser Lys Glu Asp Ala Asn Val

Phe Ala Ser Ala Met Met His Ala Leu Glu Val Leu Asn Ser Gln Glu Thr Gly Pro Thr

Leu Pro Arg Gln Asn Ser Gln Leu Pro Ala Gln Val Gln Asn Gly Pro Ser Gln Glu Glu

Leu Glu Ile Gln Arg Arg Gln Leu Gln Glu Gln Gln Arg Gln Lys Glu Leu Glu Arg Glu

Arg Leu Glu Arg Glu Arg Met Glu Arg Glu Arg Leu Glu Arg Glu Arg Leu Glu Arg

Glu Arg Leu Glu Arg Glu Arg Leu Glu Gln Glu Gln Leu Glu Arg Glu Arg Gln Glu

Arg Glu Arg Gln Glu Arg Leu Glu Arg Gln Glu Arg Leu Glu Arg Gln Glu Arg Leu

Glu Arg Gln Glu Arg Leu Asp Arg Glu Arg Gln Glu Arg Gln Glu Arg Glu Arg Leu

Glu Arg Leu Glu Arg Glu Arg Gln Glu Arg Glu Arg Gln Glu Gln Leu Glu Arg Glu

Gln Leu Glu Trp Glu Arg Glu Arg Arg Ile Ser Ser Ala Ala Ala Pro Ala Ser Val Glu

Thr Pro Leu Asn Ser Val Leu Gly Asp Ser Ser Ala Ser Glu Pro Gly Leu Gln Ala Ala

-continued

```
Ser Gln Pro Ala Glu Thr Pro Ser Gln Gln Gly Ile Val Leu Gly Pro Leu Ala Pro Pro

Pro Pro Pro Pro Leu Pro Pro Gly Pro Ala Gln Ala Ser Val Ala Leu Pro Pro Pro

Gly Pro Pro Pro Pro Pro Leu Pro Ser Thr Gly Pro Pro Pro Pro Pro Pro Pro

Leu Pro Asn Gln Val Pro Pro Pro Pro Pro Pro Ala Pro Pro Leu Pro Ala Ser

Gly Phe Phe Leu Ala Ser Met Ser Glu Asp Asn Arg Pro Leu Thr Gly Leu Ala Ala Ala

Ile Ala Gly Ala Lys Leu Arg Lys Val Ser Arg Met Glu Asp Thr Ser Phe Pro Ser Gly

Gly Asn Ala Ile Gly Val Asn Ser Ala Ser Ser Lys Thr Asp Thr Gly Arg Gly Asn Gly

Pro Leu Pro Leu Gly Gly Ser Gly Leu Met Glu Glu Met Ser Ala Leu Leu Ala Arg Arg

Arg Arg Ile Ala Glu Lys Gly Ser Thr Ile Glu Thr Glu Gln Lys Glu Asp Lys Gly Glu

Asp Ser Glu Pro Val Thr Ser Lys Ala Ser Ser Thr Ser Thr Pro Glu Pro Thr Arg Lys

Pro Trp Glu Arg Thr Asn Thr Met Asn Gly Ser Lys Ser Pro Val Ile Ser Arg Arg Asp

Ser Pro Arg Lys Asn Gln Ile Val Phe Asp Asn Arg Ser Tyr Asp Ser Leu His Arg Pro

Lys Ser Thr Pro Leu Ser Gln Pro Ser Ala Asn Gly Val Gln Thr Glu Gly Leu Asp Tyr

Asp Arg Leu Lys Gln Asp Ile Leu Asp Glu Met Arg Lys Glu Leu Thr Lys Leu Lys

Glu Glu Leu Ile Asp Ala Ile Arg Gln Glu Leu Ser Lys Ser Asn Thr Ala
```

Nucleotide sequence coding for exon 11a of the hMena 11a isoform
(SEQ ID NO: 8)
acgggattct ccaaggaaaa atcagattgt ttttgacaac aggtcctatg attcattaca cag Amino acid sequence coding for exon 11a of the hMena 11a isoform
(SEQ ID NO: 9)
Arg Asp Ser Pro Arg Lys Asn Gln Ile Val Phe Asp Asn Arg Ser Tyr Asp Ser Leu His Arg hMena 11a immunogenic peptide
(SEQ ID NO: 10)
Arg Asp Ser Pro Arg Lys Asn Gln Ile Val Phe Asp Arg Ser Tyr Asp Ser primer forward P1-ATG for amplyfing hMena
SEQ ID NO: 11
5'-CACCATGAGTGAACAGAGTATC-3' primer revers P8-stop for amplyfing hMena
SEQ ID NO: 12
5'-CTGTTCCTCTATGCAGTATTTGAC-3' primer P4-for for sequencing hMena
SEQ ID NO: 13
5'-GAGCGACTGGAACAAGAACAGCTG-3' primer P5-for for sequencing hMena
SEQ ID NO: 14
5'-GAGAGCGCAGAATATCAAGTGCTG-3' primer P6-rev for sequencing hMena
SEQ ID NO: 15
5'-GGCGATTGTCTTCTGACATGG-3' primer P7-rev for sequencing hMena
SEQ ID NO: 16
5'-GATCCCTTTTCAGCAATTC-3' sense strand siRNA for hMena deltav6
SEQ ID NO: 17
uaucaagugc uggcauuguu u antisense strand siRNA for hMena delta 6
SEQ ID NO: 18
acaaugccag cacuugauau u primer P7-for for sequencing hMena
SEQ ID NO: 19
gaattgctga aaagggatc

REFERENCES

Bear J E et al. Antagonism between Ena/VASP proteins and actin filament capping regulates fibroblast motility. Cell. 2002 May 17; 109(4):509-21

Di Modugno F, Bronzi G, Scanlan M J, et al. Human Mena protein, a serex-defined antigen overexpressed in breast cancer eliciting both humoral and CD8+ T-cell immune response. Int J Cancer 2004; 109:909-18. Di Modugno F, Mottolese M, Di Benedetto A, et al. The cytoskeleton regulatory protein hmena (ENAH) is overexpressed in human benign breast lesions with high risk of transformation and human epidermal growth factor receptor-2-positive/hormonal receptor-negative tumors. Clin Cancer Res 2006; 12:1470-8.

Di Modugno F et al. Molecular cloning of hMena (ENAH) and its splice variant hMena+11a: epidermal growth factor increases their expression and stimulates hMena+11a phosphorylation in breast cancer cell lines. Cancer Res 2007; 67:2657-65

Pino M S et al. hMena+11a isoform serves as a marker of epithelial phenotype and sensitivity to EGFR inhibition in human pancreatic cancer cell lines. Clin Cancer Res 2008; 14:4943-50

Gardina P J et al. Alternative splicing and differential gene expression in colon cancer detected by a whole genome exon array. BMC Genomics. 2006 Dec. 27; 7:325

Gertler F B et al. Mena, a relative of VASP and Drosophila Enabled, is implicated in the control of microfilament dynamics. Cell. 1996 Oct. 18; 87(2):227-39

Goswami S et al. Identification of invasion specific splice variants of the cytoskeletal protein Mena present in mammary tumor cells during invasion in vivo. Clin Exp Metastasis. 2009; 26:153-9.

McCaffrey A P, Meuse L, Pham T T, Conklin D S, Hannon G J, Kay M A. *RNA interference in adult mice*. Nature. 2002 4; 418(6893):38-9.

Krause M, et al. Ena/VASP proteins: regulators of the actin cytoskeleton and cell migration. Annu Rev Cell Dev Biol 2003; 19:541-64

Olson M F, Sahai E. The actin cytoskeleton in cancer cell motility. Clin Exp Metastasis. 2009; 26(4):273-87

Philippar U et al. A Mena invasion isoform potentiates EGF-induced carcinoma cell invasion and metastasis. Dev Cell. 2008; 15:813-28

Scott J A, et al. Mol Biol Cell 2006; 3:1085-95

Tani K et al. Abl interactor 1 promotes tyrosine 296 phosphorylation of mammalian enabled (Mena) by c-Abl kinase. J Biol Chem. 2003 Jun. 13; 278(24):21685-92

Urbanelli L et al. Characterization of human Enah gene. Biochim Biophys Acta 2006; 1759:99-107

Wang W, Goswami S, Lapidus K, et al. Identification and testing of a gene expression signature of invasive carcinoma cells within primary mammary tumors. Cancer Res 2004; 64:8585-94 2004

Wang G S, Cooper T A. Splicing in disease: disruption of the splicing code and the decoding machinery. Nat Rev Genet. 2007 October; 8(10):749-61.

Warzecha C C et al. ESRP1 and ESRP2 are epithelial cell-type-specific regulators of FGFR2 splicing. Mol Cell. 2009; 33:591-601

---

We claim:

1. A method of screening for a candidate compound that might inhibit invasive behaviour of a pre-neoplastic or neoplastic lesion or cells thereof, said method comprising:
   (a) contacting compounds with a cell line or tissue culture expressing hMenaΔv6;
   (b) measuring hMenaΔv6 expression in said cell line or tissue culture; and
   (c) selecting among the compounds at least one that reduces hMenaΔv6 expression, which is indicative that said at least one compound is a candidate compound that might inhibit invasive behaviour of a pre-neoplastic or neoplastic lesion or cells thereof.

2. The method according to claim 1, wherein said lesion is selected from the group consisting of pancreatic, breast, colorectal, gastric, ovarian, lung, prostate, urothelial, head and neck, esophageal, and skin tumours.

3. The method according to claim 2, wherein said lesion is a melanoma.

4. The method according to claim 1, wherein hMenaΔv6 expression is measured by detection of its protein product, transcription product, spliced transcript mRNA, or cDNA obtained by reverse transcription of mRNA.

5. The method according to claim 4 further comprising measuring hMena11a expression in said cell line or tissue culture, wherein lack of such expression in the presence of hMenaΔv6 expression is indicative of invasive behaviour.

6. The method according to claim 5, wherein detection of one or both hMena splicing variants is carried out by detecting corresponding protein(s) by immunohistochemistry.

7. The method according to claim 6, wherein a polyclonal or a monoclonal antibody or an immunologically active fragment thereof specific for isoform Δv6 of the hMena protein is used for hMenaΔv6 detection, and a polyclonal or a monoclonal antibody or an immunologically active fragment thereof specific for isoform 11a of the hMena protein is used for hMena11a detection.

8. The method according to claim 7, wherein said antibody or fragment thereof specific for hMenaΔv6 is specific for an epitope comprised in SEQ ID NO: 2 or SEQ ID NO: 3.

9. The method according to claim 7, wherein said antibody or fragment thereof specific for hMena11a is specific for an epitope comprised in SEQ ID NO: 9.

10. The method according to claim 3, wherein said detection is carried out by detecting transcription products comprising SEQ ID NO: 8 or fragments thereof, and transcription products comprising the junction between exon 5 and 7 of the hMena gene.

11. The method according to claim 10, wherein said detection is carried out by hybridising a mRNA or cDNA with an oligonucleotide comprising SEQ ID NO: 8 and/or its complementary sequence or a fragment thereof, and with another oligonucleotide comprising from 797 to 807 of SEQ ID NO: 1 or and/or of their complementary nucleotides in the sequence complementary to SEQ ID NO: 1.

12. The method according to claim 10, wherein said detection is carried out by amplifying mRNA or cDNA with a primer pair amplifying SEQ ID NO: 8 or a fragment thereof, and with another primer pair amplifying a fragment of SEQ ID NO: 1 comprising nucleotides from 797 to 807 of SEQ ID NO: 1.

13. A method of screening for a candidate compound, said method comprising:
   (a) contacting compounds with cells or tissue expressing hMenaΔv6;
   (b) measuring said cells or tissue, tetramers of Ena/VASP family members that contain hMenaΔv6; and
   (c) selecting among the compounds at least one that reduces tetramers that contain hMenaΔv6 interacting with other members of the Ena/VASP family, which is indicative that said at least one compound is a candidate compound that might inhibit invasive behaviour of a pre-neoplastic or neoplastic lesion or cells thereof.

14. The method according to claim 13, wherein said reduction is detected by displacement of hMenaΔv6 from tetramers in which hMenaΔv6 interacts with other hMena isoforms.

15. The method according to claim 13, wherein said lesion is selected from the group consisting of pancreatic, breast, colorectal, gastric, ovarian, lung, prostate, urothelial, head and neck, esophageal, and skin tumours including melanoma.

16. The method according to claim 15, wherein said lesion is a melanoma.

17. The method according to claim 13, wherein said cells expressing hMenaΔv6 are blood-free circulating neoplastic lesion cells.

18. The method according to claim 13, wherein said reduction is detected by displacement of hMenaΔv6 from tetramers in which hMenaΔv6 interacts with other Ena/VASP family members.

19. The method according to claim 13, wherein said reduction is detected by formation of tetramers in which hMenaΔv6 interacts with other hMena isoforms.

20. The method according to claim 13, wherein said reduction is detected by formation of tetramers in which hMenaΔv6 interacts with other of Ena/VASP family members.

* * * * *

SEQUENCE LISTING

```
<160> NUMBER OF SEQ ID NOS: 21

<210> SEQ ID NO 1
<211> LENGTH: 1602
<212> TYPE: DNA
<213> ORGANISM: Homo sapiens
<220> FEATURE:
<221> NAME/KEY: CDS
<222> LOCATION: (1)..(1602)

<400> SEQUENCE: 1 atg agt gaa cag agt atc tgt cag gca aga gct gct gtg atg gtt tat      48
Met Ser Glu Gln Ser Ile Cys Gln Ala Arg Ala Ala Val Met Val Tyr
1               5                   10                  15 gat gat gcc aat aag aag tgg gtg cca gct ggt ggc tca act gga ttc      96
Asp Asp Ala Asn Lys Lys Trp Val Pro Ala Gly Gly Ser Thr Gly Phe
                20                  25                  30 agc aga gtt cat atc tat cac cat aca ggc aac aac aca ttc aga gtg     144
Ser Arg Val His Ile Tyr His His Thr Gly Asn Asn Thr Phe Arg Val
            35                  40                  45 gtg ggc agg aag att cag gac cat cag gtc gtg ata aac tgt gcc att     192
Val Gly Arg Lys Ile Gln Asp His Gln Val Val Ile Asn Cys Ala Ile
        50                  55                  60 cct aaa ggg ttg aag tac aat caa gct aca cag acc ttc cac cag tgg     240
Pro Lys Gly Leu Lys Tyr Asn Gln Ala Thr Gln Thr Phe His Gln Trp
65                  70                  75                  80 cga gat gct aga cag gtg tat ggt ctc aac ttt ggc agc aaa gag gat     288
Arg Asp Ala Arg Gln Val Tyr Gly Leu Asn Phe Gly Ser Lys Glu Asp
                85                  90                  95 gcc aat gtc ttc gca agt gcc atg atg cat gcc tta gaa gtg tta aat     336
Ala Asn Val Phe Ala Ser Ala Met Met His Ala Leu Glu Val Leu Asn
                100                 105                 110
```

```
                                              -continued tca cag gaa aca ggg cca aca ttg cct aga caa aac tca caa cta cct      384
Ser Gln Glu Thr Gly Pro Thr Leu Pro Arg Gln Asn Ser Gln Leu Pro
            115                 120                 125 gct caa gtt caa aat ggc cca tcc caa gaa gaa ttg gaa att caa aga      432
Ala Gln Val Gln Asn Gly Pro Ser Gln Glu Glu Leu Glu Ile Gln Arg
130                 135                 140 aga caa cta caa gaa cag caa cgg caa aag gag ctg gag cgg gaa agg      480
Arg Gln Leu Gln Glu Gln Gln Arg Gln Lys Glu Leu Glu Arg Glu Arg
145                 150                 155                 160 ctg gag cga gaa aga atg gaa aga gaa agg ttg gag aga gag agg tta      528
Leu Glu Arg Glu Arg Met Glu Arg Glu Arg Leu Glu Arg Glu Arg Leu
                165                 170                 175 gaa agg gaa agg ctg gag agg gag cga ctg gaa caa gaa cag ctg gag      576
Glu Arg Glu Arg Leu Glu Arg Glu Arg Leu Glu Gln Glu Gln Leu Glu
            180                 185                 190 aga gag aga caa gaa cgg gaa cgg cag gaa cgc ctg gag cgg cag gaa      624
Arg Glu Arg Gln Glu Arg Glu Arg Gln Glu Arg Leu Glu Arg Gln Glu
        195                 200                 205 cgc ctg gag cgg cag gaa cgc ctg gag cgg cag gaa cgc ctg gat cgg      672
Arg Leu Glu Arg Gln Glu Arg Leu Glu Arg Gln Glu Arg Leu Asp Arg
    210                 215                 220 gag agg caa gaa aga caa gaa cga gag agg ctg gag aga ctg gaa cgg      720
Glu Arg Gln Glu Arg Gln Arg Glu Arg Leu Glu Arg Leu Glu Arg
225                 230                 235                 240 gag agg caa gaa agg gag cga caa gag cag tta gaa agg gaa cag ctg      768
Glu Arg Gln Glu Arg Glu Arg Gln Glu Gln Leu Glu Arg Glu Gln Leu
                245                 250                 255 gaa tgg gag aga gag cgc aga ata tca agt gct ggc att gtc ttg gga      816
Glu Trp Glu Arg Glu Arg Arg Ile Ser Ala Gly Ile Val Leu Gly
            260                 265                 270 cca ctt gca cct cca cct cct cca cca ctc cca cca ggg cct gca cag      864
Pro Leu Ala Pro Pro Pro Pro Pro Pro Leu Pro Pro Gly Pro Ala Gln
        275                 280                 285 gct tca gta gcc ctc cct cct ccc cca ggg ccc cct cca cct cct cca      912
Ala Ser Val Ala Leu Pro Pro Pro Pro Gly Pro Pro Pro Pro Pro Pro
    290                 295                 300 ctc cca tcc acc ggg cct cca ccg ccc cct cct ccc cct cct ctc cct      960
Leu Pro Ser Thr Gly Pro Pro Pro Pro Pro Pro Pro Pro Pro Leu Pro
305                 310                 315                 320 aat caa gta ccc cct cct cct cca cca cct cct gcc cca ccc ctc cct     1008
Asn Gln Val Pro Pro Pro Pro Pro Pro Pro Pro Ala Pro Pro Leu Pro
                325                 330                 335 gca tct gga ttc ttt ttg gca tcc atg tca gaa gac aat cgc cct tta     1056
Ala Ser Gly Phe Phe Leu Ala Ser Met Ser Glu Asp Asn Arg Pro Leu
            340                 345                 350 act gga ctt gca gct gca att gcc gga gca aaa ctt agg aaa gtg tca     1104
Thr Gly Leu Ala Ala Ala Ile Ala Gly Ala Lys Leu Arg Lys Val Ser
        355                 360                 365 cgg atg gag gat acc tct ttc cca agt gga ggg aat gct att ggt gtg     1152
Arg Met Glu Asp Thr Ser Phe Pro Ser Gly Gly Asn Ala Ile Gly Val
    370                 375                 380 aac tcc gcc tca tct aaa aca gat aca ggc cgt gga aat gga ccc ctt     1200
Asn Ser Ala Ser Ser Lys Thr Asp Thr Gly Arg Gly Asn Gly Pro Leu
385                 390                 395                 400 cct tta ggg ggt agt ggt tta atg gaa gaa atg agt gcc ctg ctg gcc     1248
Pro Leu Gly Gly Ser Gly Leu Met Glu Glu Met Ser Ala Leu Leu Ala
                405                 410                 415 agg agg aga aga att gct gaa aag gga tca aca ata gaa aca gaa caa     1296
Arg Arg Arg Arg Ile Ala Glu Lys Gly Ser Thr Ile Glu Thr Glu Gln
```

-continued

```
                420              425              430
aaa gag gac aaa ggt gaa gat tca gag cct gta act tct aag gcc tct    1344
Lys Glu Asp Lys Gly Glu Asp Ser Glu Pro Val Thr Ser Lys Ala Ser
            435              440              445 tca aca agt aca cct gaa cca aca aga aaa cct tgg gaa aga aca aat    1392
Ser Thr Ser Thr Pro Glu Pro Thr Arg Lys Pro Trp Glu Arg Thr Asn
450              455              460 aca atg aat ggc agc aag tca cct gtt atc tcc aga cca aaa tcc aca    1440
Thr Met Asn Gly Ser Lys Ser Pro Val Ile Ser Arg Pro Lys Ser Thr
465              470              475              480 ccc tta tca cag ccc agt gcc aat gga gtc cag acg gaa gga ctt gac    1488
Pro Leu Ser Gln Pro Ser Ala Asn Gly Val Gln Thr Glu Gly Leu Asp
                485              490              495 tat gac agg ctg aag cag gac att tta gat gaa atg aga aaa gaa tta    1536
Tyr Asp Arg Leu Lys Gln Asp Ile Leu Asp Glu Met Arg Lys Glu Leu
            500              505              510 aca aag cta aaa gaa gag ctc att gat gca atc agg cag gaa ctg agc    1584
Thr Lys Leu Lys Glu Glu Leu Ile Asp Ala Ile Arg Gln Glu Leu Ser
        515              520              525 aag tca aat act gca tag                                            1602
Lys Ser Asn Thr Ala
    530

<210> SEQ ID NO 2
<211> LENGTH: 533
<212> TYPE: PRT
<213> ORGANISM: Homo sapiens

<400> SEQUENCE: 2

Met Ser Glu Gln Ser Ile Cys Gln Ala Arg Ala Ala Val Met Val Tyr
1               5                   10                  15

Asp Asp Ala Asn Lys Lys Trp Val Pro Ala Gly Gly Ser Thr Gly Phe
            20                  25                  30

Ser Arg Val His Ile Tyr His His Thr Gly Asn Asn Thr Phe Arg Val
        35                  40                  45

Val Gly Arg Lys Ile Gln Asp His Gln Val Val Ile Asn Cys Ala Ile
    50                  55                  60

Pro Lys Gly Leu Lys Tyr Asn Gln Ala Thr Gln Thr Phe His Gln Trp
65                  70                  75                  80

Arg Asp Ala Arg Gln Val Tyr Gly Leu Asn Phe Gly Ser Lys Glu Asp
                85                  90                  95

Ala Asn Val Phe Ala Ser Ala Met Met His Ala Leu Glu Val Leu Asn
            100                 105                 110

Ser Gln Glu Thr Gly Pro Thr Leu Pro Arg Gln Asn Ser Gln Leu Pro
        115                 120                 125

Ala Gln Val Gln Asn Gly Pro Ser Gln Glu Glu Leu Glu Ile Gln Arg
    130                 135                 140

Arg Gln Leu Gln Glu Gln Gln Arg Gln Lys Glu Leu Glu Arg Glu Arg
145                 150                 155                 160

Leu Glu Arg Glu Arg Met Glu Arg Glu Arg Leu Glu Arg Glu Arg Leu
                165                 170                 175

Glu Arg Glu Arg Leu Glu Arg Glu Arg Leu Glu Gln Glu Gln Leu Glu
            180                 185                 190

Arg Glu Arg Gln Glu Arg Glu Arg Glu Arg Leu Glu Arg Gln Glu
    195                 200                 205

Arg Leu Glu Arg Gln Glu Arg Leu Glu Arg Gln Glu Arg Leu Asp Arg
    210                 215                 220
```

```
Glu Arg Gln Glu Arg Gln Glu Arg Leu Glu Arg Leu Glu Arg
225                 230                 235                 240
Glu Arg Gln Glu Arg Glu Arg Gln Glu Gln Leu Glu Arg Glu Gln Leu
                245                 250                 255
Glu Trp Glu Arg Glu Arg Arg Ile Ser Ser Ala Gly Ile Val Leu Gly
        260                 265                 270
Pro Leu Ala Pro Pro Pro Pro Pro Leu Pro Pro Gly Pro Ala Gln
            275                 280                 285
Ala Ser Val Ala Leu Pro Pro Pro Gly Pro Pro Pro Pro Pro
        290                 295                 300
Leu Pro Ser Thr Gly Pro Pro Pro Pro Pro Pro Leu Pro
305                 310                 315                 320
Asn Gln Val Pro Pro Pro Pro Pro Pro Ala Pro Pro Leu Pro
                325                 330                 335
Ala Ser Gly Phe Phe Leu Ala Ser Met Ser Glu Asp Asn Arg Pro Leu
            340                 345                 350
Thr Gly Leu Ala Ala Ala Ile Ala Gly Ala Lys Leu Arg Lys Val Ser
            355                 360                 365
Arg Met Glu Asp Thr Ser Phe Pro Ser Gly Gly Asn Ala Ile Gly Val
370                 375                 380
Asn Ser Ala Ser Ser Lys Thr Asp Thr Gly Arg Gly Asn Gly Pro Leu
385                 390                 395                 400
Pro Leu Gly Gly Ser Gly Leu Met Glu Glu Met Ser Ala Leu Leu Ala
                405                 410                 415
Arg Arg Arg Arg Ile Ala Glu Lys Gly Ser Thr Ile Glu Thr Glu Gln
            420                 425                 430
Lys Glu Asp Lys Gly Glu Asp Ser Glu Pro Val Thr Ser Lys Ala Ser
            435                 440                 445
Ser Thr Ser Thr Pro Glu Pro Thr Arg Lys Pro Trp Glu Arg Thr Asn
450                 455                 460
Thr Met Asn Gly Ser Lys Ser Pro Val Ile Ser Arg Pro Lys Ser Thr
465                 470                 475                 480
Pro Leu Ser Gln Pro Ser Ala Asn Gly Val Gln Thr Glu Gly Leu Asp
                485                 490                 495
Tyr Asp Arg Leu Lys Gln Asp Ile Leu Asp Glu Met Arg Lys Glu Leu
            500                 505                 510
Thr Lys Leu Lys Glu Glu Leu Ile Asp Ala Ile Arg Gln Glu Leu Ser
            515                 520                 525
Lys Ser Asn Thr Ala
            530

<210> SEQ ID NO 3
<211> LENGTH: 12
<212> TYPE: PRT
<213> ORGANISM: Artificial Sequence
<220> FEATURE:
<223> OTHER INFORMATION: immunogenic peptide used to obtain anti-delta
      v6 antibody

<400> SEQUENCE: 3

Glu Arg Arg Ile Ser Ser Ala Gly Ile Val Leu Gly
1               5                   10

<210> SEQ ID NO 4
<211> LENGTH: 13
<212> TYPE: PRT
```

<210> SEQ ID NO 5
<211> LENGTH: 13
<212> TYPE: PRT
<213> ORGANISM: Artificial Sequence
<220> FEATURE:
<223> OTHER INFORMATION: peptide used in affinity chromatography

<400> SEQUENCE: 4

Glu Trp Glu Arg Glu Arg Arg Ile Ser Ser Ala Ala Ala
1               5                   10

<210> SEQ ID NO 5
<211> LENGTH: 13
<212> TYPE: PRT
<213> ORGANISM: Artificial Sequence
<220> FEATURE:
<223> OTHER INFORMATION: peptide used in affinity chromatography

<400> SEQUENCE: 5

Ser Gln Gln Gly Ile Val Leu Gly Pro Leu Ala Pro Pro
1               5                   10

<210> SEQ ID NO 6
<211> LENGTH: 1776
<212> TYPE: DNA
<213> ORGANISM: Homo sapiens
<220> FEATURE:
<221> NAME/KEY: CDS
<222> LOCATION: (1)..(1776)

<400> SEQUENCE: 6

| | |
|---|---:|
| atg agt gaa cag agt atc tgt cag gca aga gct gct gtg atg gtt tat<br>Met Ser Glu Gln Ser Ile Cys Gln Ala Arg Ala Ala Val Met Val Tyr<br>1               5                   10                  15 | 48 |
| gat gat gcc aat aag aag tgg gtg cca gct ggt ggc tca act gga ttc<br>Asp Asp Ala Asn Lys Lys Trp Val Pro Ala Gly Gly Ser Thr Gly Phe<br>            20                  25                  30 | 96 |
| agc aga gtt cat atc tat cac cat aca ggc aac aac aca ttc aga gtg<br>Ser Arg Val His Ile Tyr His His Thr Gly Asn Asn Thr Phe Arg Val<br>        35                  40                  45 | 144 |
| gtg ggc agg aag att cag gac cat cag gtc gtg ata aac tgt gcc att<br>Val Gly Arg Lys Ile Gln Asp His Gln Val Val Ile Asn Cys Ala Ile<br>    50                  55                  60 | 192 |
| cct aaa ggg ttg aag tac aat caa gct aca cag acc ttc cac cag tgg<br>Pro Lys Gly Leu Lys Tyr Asn Gln Ala Thr Gln Thr Phe His Gln Trp<br>65                  70                  75                  80 | 240 |
| cga gat gct aga cag gtg tat ggt ctc aac ttt ggc agc aaa gag gat<br>Arg Asp Ala Arg Gln Val Tyr Gly Leu Asn Phe Gly Ser Lys Glu Asp<br>                85                  90                  95 | 288 |
| gcc aat gtc ttc gca agt gcc atg atg cat gcc tta gaa gtg tta aat<br>Ala Asn Val Phe Ala Ser Ala Met Met His Ala Leu Glu Val Leu Asn<br>            100                 105                 110 | 336 |
| tca cag gaa aca ggg cca aca ttg cct aga caa aac tca caa cta cct<br>Ser Gln Glu Thr Gly Pro Thr Leu Pro Arg Gln Asn Ser Gln Leu Pro<br>        115                 120                 125 | 384 |
| gct caa gtt caa aat ggc cca tcc caa gaa gaa ttg gaa att caa aga<br>Ala Gln Val Gln Asn Gly Pro Ser Gln Glu Glu Leu Glu Ile Gln Arg<br>    130                 135                 140 | 432 |
| aga caa cta caa gaa cag caa cgg caa aag gag ctg gag cgg gaa agg<br>Arg Gln Leu Gln Glu Gln Gln Arg Gln Lys Glu Leu Glu Arg Glu Arg<br>145                 150                 155                 160 | 480 |
| ctg gag cga gaa aga atg gaa aga gaa agg ttg gag aga gag agg tta<br>Leu Glu Arg Glu Arg Met Glu Arg Glu Arg Leu Glu Arg Glu Arg Leu<br>                165                 170                 175 | 528 |
| gaa agg gaa agg ctg gag agg gag cga ctg gaa caa gaa cag ctg gag<br>Glu Arg Glu Arg Leu Glu Arg Glu Arg Leu Glu Gln Glu Gln Leu Glu | 576 |

-continued

```
                180                 185                 190
aga gag aga caa gaa cgg gaa cgg cag gaa cgc ctg gag cgg cag gaa      624
Arg Glu Arg Gln Glu Arg Glu Arg Gln Glu Arg Leu Glu Arg Gln Glu
            195                 200                 205 cgc ctg gag cgg cag gaa cgc ctg gag cgg cag gaa cgc ctg gat cgg      672
Arg Leu Glu Arg Gln Glu Arg Leu Glu Arg Gln Glu Arg Leu Asp Arg
        210                 215                 220 gag agg caa gaa aga caa gaa cga gag agg ctg gag aga ctg gaa cgg      720
Glu Arg Gln Glu Arg Gln Glu Arg Glu Arg Leu Glu Arg Leu Glu Arg
225                 230                 235                 240 gag agg caa gaa agg gag cga caa gag cag tta gaa agg gaa cag ctg      768
Glu Arg Gln Glu Arg Glu Arg Gln Glu Gln Leu Glu Arg Glu Gln Leu
            245                 250                 255 gaa tgg gag aga gag cgc aga ata tca agt gct gct gcc cct gcc tct      816
Glu Trp Glu Arg Glu Arg Arg Ile Ser Ser Ala Ala Ala Pro Ala Ser
        260                 265                 270 gtt gag act cct cta aac tct gtg ctg gga gac tct tct gct tct gag      864
Val Glu Thr Pro Leu Asn Ser Val Leu Gly Asp Ser Ser Ala Ser Glu
    275                 280                 285 cca ggc ttg cag gca gcc tct cag ccg gcc gag act cca tcc caa cag      912
Pro Gly Leu Gln Ala Ala Ser Gln Pro Ala Glu Thr Pro Ser Gln Gln
290                 295                 300 ggc att gtc ttg gga cca ctt gca cct cca cct cct cca cca ctc cca      960
Gly Ile Val Leu Gly Pro Leu Ala Pro Pro Pro Pro Pro Pro Leu Pro
305                 310                 315                 320 cca ggg cct gca cag gct tca gta gcc ctc cct cct ccc cca ggg ccc     1008
Pro Gly Pro Ala Gln Ala Ser Val Ala Leu Pro Pro Pro Pro Gly Pro
            325                 330                 335 cct cca cct cct cca ctc cca tcc acc ggg cct cca ccg ccc cct cct     1056
Pro Pro Pro Pro Pro Leu Pro Ser Thr Gly Pro Pro Pro Pro Pro Pro
        340                 345                 350 ccc cct cct ctc cct aat caa gta ccc cct cct cct cca cca cct cct     1104
Pro Pro Pro Leu Pro Asn Gln Val Pro Pro Pro Pro Pro Pro Pro Pro
    355                 360                 365 gcc cca ccc ctc cct gca tct gga ttc ttt ttg gca tcc atg tca gaa     1152
Ala Pro Pro Leu Pro Ala Ser Gly Phe Phe Leu Ala Ser Met Ser Glu
370                 375                 380 gac aat cgc cct tta act gga ctt gca gct gca att gcc gga gca aaa     1200
Asp Asn Arg Pro Leu Thr Gly Leu Ala Ala Ala Ile Ala Gly Ala Lys
385                 390                 395                 400 ctt agg aaa gtg tca cgg atg gag gat acc tct ttc cca agt gga ggg     1248
Leu Arg Lys Val Ser Arg Met Glu Asp Thr Ser Phe Pro Ser Gly Gly
            405                 410                 415 aat gct att ggt gtg aac tcc gcc tca tct aaa aca gat aca ggc cgt     1296
Asn Ala Ile Gly Val Asn Ser Ala Ser Ser Lys Thr Asp Thr Gly Arg
        420                 425                 430 gga aat gga ccc ctt cct tta ggg ggt agt ggt tta atg gaa gaa atg     1344
Gly Asn Gly Pro Leu Pro Leu Gly Gly Ser Gly Leu Met Glu Glu Met
    435                 440                 445 agt gcc ctg ctg gcc agg agg aga aga att gct gaa aag gga tca aca     1392
Ser Ala Leu Leu Ala Arg Arg Arg Arg Ile Ala Glu Lys Gly Ser Thr
450                 455                 460 ata gaa aca gaa caa aaa gag gac aaa ggt gaa gat tca gag cct gta     1440
Ile Glu Thr Glu Gln Lys Glu Asp Lys Gly Glu Asp Ser Glu Pro Val
465                 470                 475                 480 act tct aag gcc tct tca aca agt aca cct gaa cca aca aga aaa cct     1488
Thr Ser Lys Ala Ser Ser Thr Ser Thr Pro Glu Pro Thr Arg Lys Pro
            485                 490                 495 tgg gaa aga aca aat aca atg aat ggc agc aag tca cct gtt atc tcc     1536
Trp Glu Arg Thr Asn Thr Met Asn Gly Ser Lys Ser Pro Val Ile Ser
```

```
          Trp Glu Arg Thr Asn Thr Met Asn Gly Ser Lys Ser Pro Val Ile Ser
                          500                 505                 510 aga cgg gat tct cca agg aaa aat cag att gtt ttt gac aac agg tcc         1584
Arg Arg Asp Ser Pro Arg Lys Asn Gln Ile Val Phe Asp Asn Arg Ser
            515                 520                 525 tat gat tca tta cac aga cca aaa tcc aca ccc tta tca cag ccc agt         1632
Tyr Asp Ser Leu His Arg Pro Lys Ser Thr Pro Leu Ser Gln Pro Ser
        530                 535                 540 gcc aat gga gtc cag acg gaa gga ctt gac tat gac agg ctg aag cag         1680
Ala Asn Gly Val Gln Thr Glu Gly Leu Asp Tyr Asp Arg Leu Lys Gln
545                 550                 555                 560 gac att tta gat gaa atg aga aaa gaa tta aca aag cta aaa gaa gag         1728
Asp Ile Leu Asp Glu Met Arg Lys Glu Leu Thr Lys Leu Lys Glu Glu
                565                 570                 575 ctc att gat gca atc agg cag gaa ctg agc aag tca aat act gca tag         1776
Leu Ile Asp Ala Ile Arg Gln Glu Leu Ser Lys Ser Asn Thr Ala
            580                 585                 590

<210> SEQ ID NO 7
<211> LENGTH: 591
<212> TYPE: PRT
<213> ORGANISM: Homo sapiens

<400> SEQUENCE: 7

Met Ser Glu Gln Ser Ile Cys Gln Ala Arg Ala Ala Val Met Val Tyr
1               5                   10                  15

Asp Asp Ala Asn Lys Lys Trp Val Pro Ala Gly Gly Ser Thr Gly Phe
            20                  25                  30

Ser Arg Val His Ile Tyr His His Thr Gly Asn Asn Thr Phe Arg Val
        35                  40                  45

Val Gly Arg Lys Ile Gln Asp His Gln Val Val Ile Asn Cys Ala Ile
    50                  55                  60

Pro Lys Gly Leu Lys Tyr Asn Gln Ala Thr Gln Thr Phe His Gln Trp
65                  70                  75                  80

Arg Asp Ala Arg Gln Val Tyr Gly Leu Asn Phe Gly Ser Lys Glu Asp
                85                  90                  95

Ala Asn Val Phe Ala Ser Ala Met Met His Ala Leu Glu Val Leu Asn
            100                 105                 110

Ser Gln Glu Thr Gly Pro Thr Leu Pro Arg Gln Asn Ser Gln Leu Pro
        115                 120                 125

Ala Gln Val Gln Asn Gly Pro Ser Gln Glu Glu Leu Glu Ile Gln Arg
    130                 135                 140

Arg Gln Leu Gln Glu Gln Arg Gln Lys Glu Leu Glu Arg Glu Arg
145                 150                 155                 160

Leu Glu Arg Glu Arg Met Glu Arg Glu Arg Leu Glu Arg Glu Arg Leu
                165                 170                 175

Glu Arg Glu Arg Leu Glu Arg Glu Arg Leu Glu Gln Glu Gln Leu Glu
            180                 185                 190

Arg Glu Arg Gln Glu Arg Glu Arg Gln Glu Arg Leu Glu Arg Gln Glu
        195                 200                 205

Arg Leu Glu Arg Gln Glu Arg Leu Glu Arg Gln Glu Arg Leu Asp Arg
    210                 215                 220

Glu Arg Gln Glu Arg Gln Glu Arg Gln Arg Leu Glu Arg Leu Glu Arg
225                 230                 235                 240

Glu Arg Gln Glu Arg Glu Arg Gln Glu Gln Leu Glu Arg Glu Gln Leu
                245                 250                 255
```

-continued

```
Glu Trp Glu Arg Arg Arg Ile Ser Ser Ala Ala Ala Pro Ala Ser
            260                 265                 270

Val Glu Thr Pro Leu Asn Ser Val Leu Gly Asp Ser Ser Ala Ser Glu
        275                 280                 285

Pro Gly Leu Gln Ala Ala Ser Gln Pro Ala Glu Thr Pro Ser Gln Gln
    290                 295                 300

Gly Ile Val Leu Gly Pro Leu Ala Pro Pro Pro Pro Pro Pro Leu Pro
305                 310                 315                 320

Pro Gly Pro Ala Gln Ala Ser Val Ala Leu Pro Pro Pro Gly Pro
                325                 330                 335

Pro Pro Pro Pro Leu Pro Ser Thr Gly Pro Pro Pro Pro Pro
            340                 345                 350

Pro Pro Pro Leu Pro Asn Gln Val Pro Pro Pro Pro Pro Pro
            355                 360                 365

Ala Pro Pro Leu Pro Ala Ser Gly Phe Phe Leu Ala Ser Met Ser Glu
    370                 375                 380

Asp Asn Arg Pro Leu Thr Gly Leu Ala Ala Ile Ala Gly Ala Lys
385                 390                 395                 400

Leu Arg Lys Val Ser Arg Met Glu Asp Thr Ser Phe Pro Ser Gly Gly
                405                 410                 415

Asn Ala Ile Gly Val Asn Ser Ala Ser Ser Lys Thr Asp Thr Gly Arg
                420                 425                 430

Gly Asn Gly Pro Leu Pro Leu Gly Gly Ser Gly Leu Met Glu Glu Met
            435                 440                 445

Ser Ala Leu Leu Ala Arg Arg Arg Ile Ala Glu Lys Gly Ser Thr
450                 455                 460

Ile Glu Thr Glu Gln Lys Glu Asp Lys Gly Glu Asp Ser Glu Pro Val
465                 470                 475                 480

Thr Ser Lys Ala Ser Ser Thr Ser Thr Pro Glu Pro Thr Arg Lys Pro
                485                 490                 495

Trp Glu Arg Thr Asn Thr Met Asn Gly Ser Lys Ser Pro Val Ile Ser
            500                 505                 510

Arg Arg Asp Ser Pro Arg Lys Asn Gln Ile Val Phe Asp Asn Arg Ser
        515                 520                 525

Tyr Asp Ser Leu His Arg Pro Lys Ser Thr Pro Leu Ser Gln Pro Ser
    530                 535                 540

Ala Asn Gly Val Gln Thr Glu Gly Leu Asp Tyr Asp Arg Leu Lys Gln
545                 550                 555                 560

Asp Ile Leu Asp Glu Met Arg Lys Glu Leu Thr Lys Leu Lys Glu Glu
                565                 570                 575

Leu Ile Asp Ala Ile Arg Gln Glu Leu Ser Lys Ser Asn Thr Ala
            580                 585                 590
```

<210> SEQ ID NO 8
<211> LENGTH: 63
<212> TYPE: DNA
<213> ORGANISM: Homo sapiens

<400> SEQUENCE: 8
acgggattct ccaaggaaaa atcagattgt ttttgacaac aggtcctatg attcattaca    60
cag                                                                 63

<210> SEQ ID NO 9
<211> LENGTH: 21
<212> TYPE: PRT

<213> ORGANISM: Homo sapiens

<400> SEQUENCE: 9

Arg Asp Ser Pro Arg Lys Asn Gln Ile Val Phe Asp Asn Arg Ser Tyr
1               5                   10                  15

Asp Ser Leu His Arg
            20

<210> SEQ ID NO 10
<211> LENGTH: 17
<212> TYPE: PRT
<213> ORGANISM: Homo sapiens

<400> SEQUENCE: 10

Arg Asp Ser Pro Arg Lys Asn Gln Ile Val Phe Asp Arg Ser Tyr Asp
1               5                   10                  15

Ser

<210> SEQ ID NO 11
<211> LENGTH: 22
<212> TYPE: DNA
<213> ORGANISM: Artificial Sequence
<220> FEATURE:
<223> OTHER INFORMATION: forward primer for amplifying hMena

<400> SEQUENCE: 11
caccatgagt gaacagagta tc                                        22

<210> SEQ ID NO 12
<211> LENGTH: 24
<212> TYPE: DNA
<213> ORGANISM: Artificial Sequence
<220> FEATURE:
<223> OTHER INFORMATION: reverse primer for amplifying hMena

<400> SEQUENCE: 12
ctgttcctct atgcagtatt tgac                                      24

<210> SEQ ID NO 13
<211> LENGTH: 24
<212> TYPE: DNA
<213> ORGANISM: Artificial Sequence
<220> FEATURE:
<223> OTHER INFORMATION: primer for sequencing hMena

<400> SEQUENCE: 13
gagcgactgg aacaagaaca gctg                                      24

<210> SEQ ID NO 14
<211> LENGTH: 24
<212> TYPE: DNA
<213> ORGANISM: Artificial Sequence
<220> FEATURE:
<223> OTHER INFORMATION: primer for sequencing hMena

<400> SEQUENCE: 14
gagagcgcag aatatcaagt gctg                                      24

<210> SEQ ID NO 15
<211> LENGTH: 21
<212> TYPE: DNA
<213> ORGANISM: Artificial Sequence
<220> FEATURE:
<223> OTHER INFORMATION: primer for sequencing hMena

```
<400> SEQUENCE: 15
ggcgattgtc ttctgacatg g                                          21

<210> SEQ ID NO 16
<211> LENGTH: 19
<212> TYPE: DNA
<213> ORGANISM: Artificial Sequence
<220> FEATURE:
<223> OTHER INFORMATION: primer for sequencing hMena

<400> SEQUENCE: 16
gatccctttt cagcaattc                                             19

<210> SEQ ID NO 17
<211> LENGTH: 21
<212> TYPE: RNA
<213> ORGANISM: Artificial Sequence
<220> FEATURE:
<223> OTHER INFORMATION: sense strand siRNA for hMena delta v6

<400> SEQUENCE: 17
uaucaagugc uggcauuguu u                                          21

<210> SEQ ID NO 18
<211> LENGTH: 21
<212> TYPE: RNA
<213> ORGANISM: Artificial Sequence
<220> FEATURE:
<223> OTHER INFORMATION: anti sense strand siRNA for hMena delta v6

<400> SEQUENCE: 18
acaaugccag cacuugauau u                                          21

<210> SEQ ID NO 19
<211> LENGTH: 19
<212> TYPE: DNA
<213> ORGANISM: Artificial Sequence
<220> FEATURE:
<223> OTHER INFORMATION: primer for sequencing hMena

<400> SEQUENCE: 19
gaattgctga aaagggatc                                             19

<210> SEQ ID NO 20
<211> LENGTH: 30
<212> TYPE: DNA
<213> ORGANISM: Artificial Sequence
<220> FEATURE:
<223> OTHER INFORMATION: forward primer for detection of hMena splicing
      variants

<400> SEQUENCE: 20
gctggaatgg gagagagagc gcagaatatc                                 30

<210> SEQ ID NO 21
<211> LENGTH: 30
<212> TYPE: DNA
<213> ORGANISM: Artificial Sequence
<220> FEATURE:
<223> OTHER INFORMATION: reverse primer for detection of hMena splicing
      variants

<400> SEQUENCE: 21
gtcaagtcct tccgtctgga ctccattggc                                 30
```